US012696860B2

(12) United States Patent
Messmer

(10) Patent No.: US 12,696,860 B2
(45) Date of Patent: Aug. 4, 2026

(54) PENNYCRESS VARIETIES WITH IMPROVED SHATTER RESISTANCE AND EARLY MATURITY

(71) Applicant: COVERCRESS INC., St. Louis, MO (US)

(72) Inventor: Mark Messmer, St. Louis, MO (US)

(73) Assignee: CoverCress Inc., St. Louis, MO (US)

( * ) Notice: Subject to any disclaimer, the term of this patent is extended or adjusted under 35 U.S.C. 154(b) by 160 days.

(21) Appl. No.: 18/501,791

(22) Filed: Nov. 3, 2023

(65) Prior Publication Data

US 2024/0147929 A1     May 9, 2024

Related U.S. Application Data

(60) Provisional application No. 63/382,351, filed on Nov. 4, 2022, provisional application No. 63/382,369, filed on Nov. 4, 2022.

(51) Int. Cl.
*A01H 6/20* (2018.01)
*A01H 5/10* (2018.01)

(52) U.S. Cl.
CPC ................. *A01H 6/20* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 7,528,294 B2 | 5/2009 | Yanofsky et al. | |
| 8,809,635 B2 | 8/2014 | Laga et al. | |
| 10,709,151 B2 | 7/2020 | Ulmasov et al. | |
| 10,988,772 B2 | 4/2021 | Ulmasov et al. | |
| 11,408,008 B2 | 8/2022 | Marks et al. | |
| 2017/0055480 A1 | 3/2017 | Laga et al. | |
| 2018/0148735 A1 | 5/2018 | Begemann et al. | |
| 2019/0053458 A1* | 2/2019 | Marks | A01H 6/20 |
| 2019/0082718 A1* | 3/2019 | Ulmasov | A23K 50/75 |
| 2019/0225977 A1 | 7/2019 | Ulmasov et al. | |
| 2020/0131523 A1 | 4/2020 | Marks et al. | |
| 2022/0298519 A1 | 9/2022 | Atwood et al. | |
| 2023/0263190 A1 | 8/2023 | Ulmasov et al. | |
| 2023/0265450 A1 | 8/2023 | Ulmasov et al. | |

OTHER PUBLICATIONS

Applying for a Plant Variety Certificate of Protection (https://www.ams.usda.gov/services/pvpo/application-help/apply; pp. 1-3).*

UPOV, pp. 1-13, 2017.*
Ex Parte C, pp. 1-11, 1992.*
Ex parte McGowen, pp. 1-21, Appeal No. 2019-006060.*
Haun et al., (Plant physiol., 155:645-655, 2011).*
Großkinsky et al. (J exp. biol., 66:5429-5440, 2015).*
Chopra et al., "Identification and stacking of crucial traits required for the domestication of pennycress," Nature Food, Jan. 2020, vol. 1, pp. 84-91.
Chopra et al., "Translational genomics using *Arabidopsis* as a model enables the characterization of pennycress genes through forward and reverse genetics," The Plant Journal, Dec. 2018, vol. 96, pp. 1093-1105.
Dorn et al., "A draft genome of field pennycress (*Thlaspi arvense*) provides tools for the domestication of a new winter biofuel crop," DNA Research, Apr. 2015, vol. 22, No. 2, pp. 121-131.
Garcia Navarrete et al., "Natural variation and improved genome annotation of the emerging biofuel crop field pennycress (*Thlaspi arvense*)," G3, Jun. 2022 , vol. 12, No. 6, 11 pages.
Kagale et al., "The emerging biofuel crop Camelina sativa retains a highly undifferentiated hexaploid genome structure," Nature Communications, Apr. 2014, vol. 5, No. 3706, 11 pages.
Liljegren et al., "Control of Fruit Patterning in Arabidopsis by Indehiscent," Cell, Mar. 2004, vol. 116, pp. 843-853.
Marks, M., "Advancing Field Pennycress as a New Oilseed Biodiesel Feedstock that does not Require New Land Commitments," National Institute of Food and Agriculture, 2014 [retrieved on Apr. 23, 2024]. Retrieved from the Internet: <URL: https://portal.nifa.usda.gov/web/crisprojectpages/1004021-advancing-field-pennycress-as-a-new-oilseed-biodiesel-feedstock-that-does-not-require-new-land-commitments.html>, 13 pages.
Nunn et al., "Chromosome-level Thlaspi arvense genome provides new tools for translational research and for a newly domesticated cash cover crop of the cooler climates," Plant Biotechnology Journal, May 2022, vol. 20, pp. 944-963.
Sedbrook et al., "New approaches to facilitate rapid domestication of a wild plant to an oilseed crop: Example pennycress (*Thlaspi arvense* L.)," Plant Science, Oct. 2014, vol. 227, pp. 122-132.
Zhai et al., "CRISPR/Cas9-mediated genome editing reveals differences in the contribution of Indehiscent homologues to pod shatter resistance in *Brassica napus* L.," Theoretical Applied Genetics, Apr. 2019, 13 pages.

* cited by examiner

*Primary Examiner* — Vinod Kumar
(74) *Attorney, Agent, or Firm* — Klarquist Sparkman, LLP

(57) ABSTRACT

Provided herein are materials and methods for developing elite or elite commercial varieties using the *Thlaspi arvense* cultivar 2032 and variety 182002-B-B-31, which demonstrate an improved shatter resistance trait and/or an early maturation trait. The use of these cultivars together with other plants and plant materials in the Brassicaceae family to develop additional varieties having the shatter resistance trait and/or early maturation trait are provided. Methods of gene editing, breeding, and using the same in breeding program are also provided.

7 Claims, No Drawings

PENNYCRESS VARIETIES WITH IMPROVED SHATTER RESISTANCE AND EARLY MATURITY

CROSS REFERENCE TO RELATED APPLICATIONS

This application claims priority under 35 U.S.C. § 119 to provisional patent application U.S. Ser. No. 63/382,351, filed Nov. 4, 2022, and to provisional patent application U.S. Ser. No. 63/382,369 filed Nov. 4, 2022. The provisional patent applications are herein incorporated by reference in their entireties, including without limitation, the specification, claims, and abstract, as well as any figures, tables, appendices, biological sequences, biological sequence listings, or drawings thereof.

TECHNICAL FIELD

The disclosure relates to materials and methods for developing elite or elite commercial varieties using *Thlaspi arvense* cultivar designated 2032 and variety designated 182002-B-B-31, which have a reduced seedpod shatter trait (RSS) trait and/or an early maturity (EM) trait. The disclosure further relates to the use of these cultivars with other plants and plant materials in the Brassicaceae family to develop additional varieties having the shatter resistance trait and/or early maturity trait. Methods of gene editing, breeding, and using the same in breeding program are also provided.

TECHNICAL BACKGROUND

Global grain demand continues to rise as the uses of grains are increasingly diversified across not only human food supplies but animal feed, bioplastics, biofuels, and other industrial products. However, the global food system, remains extremely dependent on just a handful of mass-produced crops, such as wheat, rice, corn, and soybeans. Dependence on these crops renders global grain and crop systems extremely vulnerable to supply chain and distribution issues caused by climate changes, disease, and geopolitical problems. Further, no or minimal rotation of crops leaves farmland vulnerable to nutrient leaching and soil erosion, problems which threaten future yield and undermine both the sustainability of farming practices and the health of rural regions.

These problems could be addressed in whole or in part by the diversification of crops and particularly crops that do not impact the yield of major crops such as corn and soybeans. Various cover crops have been utilized to address at least the issues of soil quality. For example, across the United States, millions of acres of farmland are rotated between maize (*Zea mays* L.) and soybeans (*Glycine max* (L.) Merr.). A small percentage of this land is protected by a cover crop, such as winter field beans or clover, particularly in the fallow period between the fall harvest period and the following spring and/or summer planting. Although traditional cover crops provide winter soil protection and can restore soil nutrients, they suffer from a number of drawbacks such as overwintering or winterkill (when winter survival was desired), contamination of the following crop, reseeding and competition with crops, and the added cost of growing a new crop for no direct profit.

Members of the Brassicaceae family, and particularly the *Thlaspi* family (such as pennycress) provide a unique opportunity to improve the sustainability of current farming practices while also increasing farm profit. Pennycress plants can be grown in the interval between corn harvest and a subsequent soybean planting season, thereby minimizing the potential for reduced yield of summer crops. Pennycress also produces a very high yield of seeds and seed oil that can be sold as a profitable crop to the animal feed, biofuel, and bioplastics industries.

However, many pennycress varieties, particularly wild strains, are hampered by seed pods that readily break open (i.e., shatter) when mature, resulting in significant pre-harvest seed loss. Pod shattering results in about 20% of the seeds falling to the ground before they can be harvested. Loss-of-function modifications in certain pennycress genes, such as the SPATULA (SPT), ALCATRAZ (ALC), INDE-HISCENT (IND), SHATTERPROOF (SHP; e.g., SHP1 and SHP2), PINOID (PID), DZ POLYGALACTURONASE (ADPG; e.g., ADPG1 and ADPG2), and/orINDEHISCENT (IND) genes can result in a reduced seedpod shatter phenotype as compared to corresponding wild type pennycress plants (see, e.g., U.S. Pat. Pub. No. 2019/0053458 which is incorporated by reference). However, although manipulation of IND gene expression can result in plants having the reduced pod shatter trait, undesirable agronomic performance has been observed in plants having complete loss of function. In particular, genetic manipulation and/or knock-out of certain pennycress genes can reduce pod shatter "too much" in that it may be too difficult to break the pods open for commercial harvest (see, e.g., U.S. Pat. No. 8,809,635, which is herein incorporated by reference).

Maturation represents another hurdle to the successful use of pennycress varieties as a profitable cover crop. Pennycress is typically planted any time between the end of August through the third week in October in the U.S. Midwest region. Harvesting generally occurs between May and mid-June, which is late in the spring planting season. Maturation earlier in spring would be more desirable in order to accommodate the traditional summer crop planting season in spring.

There is therefore a need to develop various species in the Brassicaceae family including *Brassica napus*, *Brassica carinata*, *Camelina sativa*, and *Thlaspi* species such as *Thlaspi arvense*, *Thlaspi alliaceum*, *Thlaspi perforliatum*, *Thlaspi californicum*, *Thlaspi articum*, *Thlaspi cyprium*, *Thlaspi alpestre*, *Thlaspi kochianum*, *Thlaspi macrophyllum*, and *Thlaspi bellidifolium*, which exhibit early maturity and/or shatter resistance to a degree sufficient to prevent loss of harvest without also causing undesirable agronomic characteristics.

These and other objects, advantages, and features of the present disclosure will become apparent from the following specification taken in conjunction with the claims set forth herein.

SUMMARY

The present disclosure relates to elite or commercially elite *Thlaspi* varieties comprising a reduced seedpod shatter trait and/or early maturity trait of *Thlaspi arvense* cultivar 2032, representative seed of *Thlaspi arvense* cultivar 2032 having been deposited under NCMA Accession Number 202210002. According to some embodiments, the variety lacks the black seed, high fiber, increased lodging, and/or reduced yield traits of *Thlaspi arvense* cultivar 2032. In an embodiment, the trait is reduced seed pod shattering, early maturity, or a combination thereof.

The present disclosure also provides for seed, plants and plant parts of the elite or commercially elite *Thlaspi* varieties comprising a reduced seedpod shatter trait and/or early maturity trait of *Thlaspi arvense* cultivar 2032, representative seed of *Thlaspi arvense* cultivar 2032 having been deposited under NCMA Accession Number 202210002. In an embodiment, the part comprises a microspore, pollen, ovary, ovule, embryo sac, egg cell, cutting, root, stem, cell or protoplast.

Tissue cultures of regenerable cells or protoplasts from these plants are also provided. In an embodiment, the cells or protoplasts of the tissue culture are derived from a tissue comprising a leaf, pollen, embryo, cotyledon, hypocotyl, meristematic cell, root, root tip, anther, flower, seed or stem.

According to an embodiment, the variety is 182002-B-B-31, representative seed of *Thlaspi arvense* variety 182002-B-B-31 having been deposited under NCMA Accession Number 202210001.

Further disclosed herein are methods for producing an elite *Thlaspi* plant variety comprising a reduced seedpod shatter trait and/or an early maturity trait, the method comprising: (a) crossing a plant of *Thlaspi arvense* cultivar 2032, representative seed of *Thlaspi arvense* cultivar 2032 having been deposited under NCMA Accession Number 202210002 with a second *Thlaspi* plant from a wild cultivar or an elite or elite commercial variety lacking the reduced seedpod shatter trait and/or an early maturity trait, to create population of progeny plants, (b) selecting from said progeny plants a plant with a reduced seedpod shatter and/or early maturity, and (c) repeating steps a and b for a sufficient number of times so that an elite variety is created with reduced seedpod shatter and/or early maturity. In an embodiment, the trait is reduced seed pod shattering, early maturity, or a combination thereof.

Also provided are methods of producing a *Thlaspi* variety with reduced seed pod shattering and/or early maturity comprising obtaining a plant of *Thlaspi arvense* cultivar 2032, representative seed of the same having been deposited under NCMA Accession Number 202210002 and using the same as a source of breeding material in a plant breeding program. In an embodiment, the trait is reduced seed pod shattering, early maturity, or a combination thereof.

Disclosed herein are elite or commercially elite *Thlaspi* varieties with reduced pod shattering, and/or early maturity said variety having an ancestor thereof that is the cultivar of 2032, representative seed of which has been deposited under NCMA Accession Number 202210002. In an embodiment, the trait is reduced seed pod shattering, early maturity, or a combination thereof.

Relatedly, disclosed herein are plants and plant parts of elite or commercially elite *Thlaspi* varieties with reduced pod shattering, and/or early maturity said variety having an ancestor thereof that is the cultivar of 2032, representative seed of which has been deposited under NCMA Accession Number 202210002. In an embodiment, the plant part comprises a microspore, pollen, ovary, ovule, embryo sac, egg cell, cutting, root, stem, cell or protoplast.

Also disclosed are tissue cultures of regenerable cells or protoplasts from the plants. In an embodiment, the cells or protoplasts of the tissue culture are derived from a tissue comprising a leaf, pollen, embryo, cotyledon, hypocotyl, meristematic cell, root, root tip, anther, flower, seed or stem.

Disclosed herein are methods for obtaining a genetic marker for the trait of reduced seed pod shattering and/or early maturity comprising: isolating nucleic acids from seed of Brassicaceae variety 2032, representative seed of the variety having been deposited under NCMA Accession Number 202210002 and identifying the genetic marker that is associated with the trait of reduced shatter and/or early maturity.

Further provided are methods of introgressing the trait of reduced seed pod shattering and/or early maturity into a plant variety comprising: performing marker assisted selection with the genetic marker obtained by isolating nucleic acids from seed of Brassicaceae variety 2032, representative seed of the variety having been deposited under NCMA Accession Number 202210002 and identifying the genetic marker that is associated with the trait of reduced shatter and/or early maturity.

Disclosed herein are methods for producing a progeny plant of Brassicaceae variety 2032 with reduced seed shatter and/or early maturity for use in a plant breeding program comprising:

crossing a plant of Brassicaceae variety 2032, representative seed of the variety having been deposited under NCMA Accession Number 202210002 with itself or with another plant; harvesting the resultant seed; growing the seed to produce a progeny plant; and selecting a progeny plant with the trait of reduced seed shatter and/or an early maturity. Progeny plants produced by this method are also encompassed by the disclosure, wherein the progeny plant has reduced seedpod shatter and/or early maturity as compared to a wild type Brassicaceae plant. Relatedly seeds produced from the progeny plants and plants from these seeds are encompassed by the disclosure.

Disclosed herein are methods for producing a Brassicaceae variety 2032-derived seed for use in a breeding program comprising: (a) crossing a plant of Brassicaceae variety 2032, representative seed of the variety having been deposited under NCMA Accession Number 202210002, with itself or a second plant, (b) harvesting the seed therefrom and planting said seed to create said population of plants. In some embodiments, the method further comprises (c) crossing a plant grown from a Brassicaceae variety 2032-derived seed with itself or with a second plant to yield an additional Brassicaceae variety 2032-derived seed, (d) growing the additional Brassicaceae variety 2032-derived seed of step (c) to yield an additional Brassicaceae variety 2032-derived plant, (e) repeating the crossing and growing of steps (c) and (d) for an additional 1-10 or 1-15 generations to generate one or more further Brassicaceae variety 2032-derived plants, and (f) generating a seed of a Brassicaceae variety 2032-derived plant.

Also disclosed are methods for developing a Brassicaceae variety in a Brassicaceae plant breeding program comprising; applying plant breeding techniques comprising recurrent selection, backcrossing, pedigree breeding, marker enhanced selection, gene editing, or transformation to a *Thlaspi arvense* cultivar 2032 plant or *Thlaspi arvense* cultivar 2032 derived-plant, or its parts, wherein application of the techniques results in development of a Brassicaceae variety. In an embodiment, the Brassicaceae variety is s a variety of a *Thlaspi* genus. In a further embodiment, the Brassicaceae variety is a variety of a *Thlaspi arvense* species.

The disclosure also relates to methods of producing a commodity plant product, comprising: obtaining the plant of an elite or commercially elite *Thlaspi* variety comprising a reduced seedpod shatter trait and/or early maturity trait of *Thlaspi arvense* cultivar 2032, representative seed of *Thlaspi arvense* cultivar 2032 having been deposited under NCMA Accession Number 202210002, or a plant part thereof, and producing the commodity plant product from the plant or plant part thereof, wherein the commodity plant product is an oil, biodegradable plastic, lubricant, biofuel, food or feed product, medicinal product, or a combination thereof.

While multiple embodiments are disclosed, still other embodiments of the present disclosure will become apparent based on the detailed description, which shows and describes illustrative embodiments of the disclosure. The foregoing summary is illustrative only and is not intended to be in any way limiting. In addition to the illustrative aspects, embodiments, and features described above, further aspects, embodiments, and features of the present technology are apparent from the following drawings and the detailed description, which shows and describes illustrative embodiments of the present technology. Each feature of the technology described herein may be combined with any one or more other features of the disclosure, e.g., the methods may be used with any composition described herein. Accordingly, the detailed description is to be regarded as illustrative and not restrictive.

DETAILED DESCRIPTION

Elite commercial varieties and elite varieties of the Brassicaceae family, particularly of the *Thlaspi* genus are provided, wherein the varieties are developed using the cultivar designated 2032 and the variety designated 182002-B-B-31 as a source of genetic material. Seeds of the variety and progeny thereof, plants of the variety and progeny thereof, and methods for producing plants by crossing each cultivar with itself or another plant (whether by use of male sterility or open pollination) and methods for producing a plant containing in its genetic material one or more genes providing the reduced shatter trait are provided. Seeds, plants, and plant parts produced by crossing each cultivar with another line are also provided.

It is an advantage that the cultivars, elite commercial varieties, elite varieties, progeny, plants, plant parts, seeds, and other plant material herein have a reduced shatter trait and/or early maturity.

The embodiments of this disclosure are not limited to particular types of compositions or methods, which can vary. It is further to be understood that all terminology used herein is to describe particular embodiments only and is not intended to be limiting in any manner or scope. For example, as used in this specification and the appended claims, the singular forms "a," "an" and "the" can include plural referents unless the context indicates otherwise. Unless indicated otherwise, "or" or "and/or" can mean any one alone or any combination thereof, e.g., "A, B, or C" means the same as any of A alone, B alone, C alone, "A and B," "A and C," "B and C" or "A, B, and C." Further, all units, prefixes, and symbols may be denoted in its SI accepted form.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, a description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6, and decimals and fractions, for example, 1.2, 3.8, $1'_2$, and 4% This applies regardless of the breadth of the range.

In the description that follows, a number of terms are used. In order to aid in a clear and consistent understanding of the disclosure, the following definitions are provided.

The terms "a," "an," and "the" include both singular and plural referents.

The term "or" is synonymous with "and/or" and means any one member or combination of members of a particular list.

The term "about," as used herein, refers to variation in the numerical quantity that can occur, for example, through typical measuring techniques and equipment, with respect to any quantifiable variable, including, but not limited to, mass, volume, time, temperature, pH, reflectance, whiteness, etc. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

As used herein, the term "alleles" refers to alternate forms of a DNA sequence at a genetic locus, that is, a position on a chromosome of a gene or other chromosome marker.

As used herein, the term "cultivar" refers to a plant that has been cultivated. A cultivar is generally developed using crossing, selfing, and/or selection and is maintained by any suitable method of propagation, through open pollination, selfing, or the like. Details of cultivar development can be found in "Principles of Cultivar Development" by Fehr, Macmillan Publishing Company (1993), which is herein incorporated by reference in its entirety.

As used herein, the terms "elite," "elite variety," and "elite line" or "elite plant" refer to any line or plant that has resulted from breeding and/or gene editing and selection for one or more trait improvements (e.g., desirable agronomic performance (typically commercial production) or superior grain quality). Generally, individuals in a line have similar parentage and one or more similar traits. In some cases, an "elite line" or "elite variety" can be an agronomically or otherwise superior line or variety that has resulted from several or many cycles of breeding and selection for one or more trait improvements (e.g., superior agronomic performance or superior grain quality). An "elite inbred line" is an elite line that is an inbred, and that has been shown to be useful for producing sufficiently high yielding and agronomically fit hybrid varieties (an "elite hybrid variety"). Similarly, "elite germplasm" is a germplasm resulting from breeding and selection for desirable agronomic performance (typically commercial production). Such germplasm may be agronomically superior germplasm, derived from and/or capable of giving rise to a plant with superior agronomic performance, such as an existing or newly developed elite line of *Brassica* (e.g., pennycress). "Commercially elite," "commercially elite plants," "commercially elite seed," "elite commercial," "elite commercial plants," "elite commercial seed," or "elite commercial varieties" are elite varieties which can be used by growers to produce a profitable crop, which is purchased (e.g., as seed) for use by a grower to produce a crop, or for which a user of the crop pays for access to the seed.

As used herein, the term "fatty acid content" relates to the percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length.

As used herein, a "frameshift mutation" refers to a mutation in a nucleic acid sequence that results in the wild-type reading frame being shifted to different reading frame such that translation of an mRNA having a frameshift mutation results in a departure from the wild-type reading frame.

As used herein, "F #" denotes the filial generation, and the # is the generation number, such as $F_1$, $F_2$, $F_3$, etc. Accordingly, "$F_1$ Hybrid" refers to the first-generation progeny of the cross of two non-isogenic plants.

"Gene". As used herein, "gene" refers to a segment of nucleic acid comprising an open reading frame. A gene can be introduced into a genome of a species, whether from a different species or from the same species, using transformation or various breeding methods.

As used herein, "gene activity" comprises any measure of gene function. Gene activity measures thus include measures of gene-mediated phenotypes (e.g., pod shatter resistance and undesirable agronomic traits) and/or gene-encoded protein activity (e.g., transcriptional activation activity). In certain embodiments, transcriptional activation activity can be assayed by monitoring expression of genes that are regulated by the gene with transcriptional activation activity.

"Gene silencing" refers to the interruption or suppression of the expression of a gene, typically at the level of transcription or translation.

The term "genotype" refers to the genetic constitution of a cell or organism.

"Herbicide resistance" as used herein describes resistance of various herbicides when applied at standard recommended application rates.

"Inbred line" as used herein, refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

As used herein, the term "IND" refers to a wild-type INDEHISCENT gene or protein while the term "ind" refers to a mutant INDEHISCENT gene or protein. The term ind1-4 refers to a particular recessive ind1 allele found in the 2032 cultivar.

As used herein, the terms "include," "includes," and "including" are to be construed as at least having the features to which they refer while not excluding any additional unspecified features.

The term "Linkage" refers to a phenomenon wherein alleles on the same chromosome tend to segregate together more often than expected by chance if their transmission was independent.

"Linkage disequilibrium" refers to a phenomenon wherein alleles tend to remain together in linkage groups when segregating from parents to offspring, with a greater frequency than expected from their individual frequencies.

The term "locus" refers to a specific location on a chromosome."

As used herein, the term "locus conversion" refers to plants within a variety that have been modified in a manner that retains the overall genetics of the variety and further comprises one or more loci with a specific desired trait, such as male sterility, insect, disease or herbicide resistance, or low erucic acid content. Examples of single locus conversions include mutant genes, transgenes and native traits finely mapped to a single locus. One or more locus conversion traits may be introduced into a single canola variety.

"Maturity" as used herein is defined as the stage where pod seed fill has been completed, 90 percent of the pods have turned to a tan to light brown coloration with the remainder being yellow, and seed moisture is less than about 18% or 20% by weight. At this point, most, if not all, of the leaves have been lost, but the stems may range from green to brown. -, At this point the plant is considered to be dead and the life cycle completed.

The term "oil content" refers to the typical percentage by weight oil present in the mature whole dried seeds is determined by ISO 10565:1993 Oilseeds Simultaneous determination of oil and water—Pulsed NMR method. Also, oil could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, flowers, pods, or stalks. In contrast, some plant cells are not capable of being regenerated to produce plants and are referred to herein as "non-regenerable" plant cells.

"Ploidy" refers to the number of chromosomes exhibited by the line, for example diploid or tetraploid.

The term "protein content" refers to the typical percentage by weight of protein in the oil free meal of the mature whole dried seeds is determined by AOCS Official Method Ba 4e-93 Combustion Method for the Determination of Crude Protein. Also, protein could be analyzed using NIR (Near Infrared) spectroscopy as long as the instrument is calibrated according to the manufacturer's specifications, reference AOCS Procedure Am 1-92 Determination of Oil, Moisture and Volatile Matter, and Protein by Near-Infrared Reflectance.

"Resistance" as used herein refers to the ability of a plant to withstand exposure to an insect, disease, herbicide, temperature extremes, or other condition. A resistant plant variety or hybrid will have a level of resistance higher than a comparable wild-type variety or hybrid. "Tolerance" is a term commonly used in crops such as canola, soybean, and sunflower affected by an insect, disease, such as *Sclerotinia*, herbicide, or other condition and is used to describe an improved level of field resistance.

"Seed pods" are the specialized structures that contain the seed(s) during development and maturation into grain. Seed pods serve as the seeds' protection from the external environment and provide the energy and nutrients for seed development. When the seed reaches full maturity, the seed pod becomes dry and brittle and having lost all its chlorophyll assumes a yellow coloration. At this time as well the seed pod becomes susceptible to dehiscence, the physical opening of the structure, allowing release of the mature seed.

The term "silique" as used herein refers to the seedpod of plants of the Brassicaceae family that splits open when mature. "Silique" is used interchangeably with "pod" and "seed pod" herein.

As used herein, "shatter resistance," "reduced shatter," "reduced shatter trait," and "reduced seedpod shatter" refer to resistance to silique shattering observed at seed maturity. In particular, plants possessing this trait have seedpods requiring a greater amount of force to break open than an amount of force needed to break open a wild type seedpod.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants.

The term "transgene" refers to a nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

As used herein, the term "variety" means a group of similar plants that by one or more structural features, genetic features, and/or performance can be distinguished from other varieties within the same species. In certain embodiments, the term variety refers to the botanical taxonomic designation whereby variety is ranked below species or subspecies, as well as the legal definition whereby the term "variety" refers to a commercial plant that is protected under the terms outlined in the International Convention for the Protection of New Varieties of Plants.

Brassicaceae Cultivars

Disclosed herein are Brassicaceae varieties, particularly elite or commercially elite varieties having a reduced seed pod shattering trait and/or an early maturity trait. Further disclosed are *Thlaspi arvense* varieties having a reduced seed pod shattering trait and/or an early maturation trait.

More particularly, the disclosure provides for an elite or commercially elite *Thlaspi* variety comprising a reduced seedpod shatter trait and/or early maturity trait of *Thlaspi arvense* cultivar 2032, representative seed of *Thlaspi arvense* cultivar 2032 having been deposited under NCMA Accession Number 202210002. In some embodiments, the variety lacks the increased lodging and reduced yield traits of *Thlaspi arvense* cultivar 2032. In certain embodiments, the variety lacks the increased lodging, wild-type dark seed, wild-type seed fiber content, wild-type seed sinigrin content, and/or wild-type seed erucic acid content traits of *Thlaspi arvense* cultivar 2032. In an embodiment, trait is reduced seed pod shattering. In an alternative embodiment, the trait is early maturity. In a still further embodiment, the trait is reduced seed pod shattering and early maturity. Relatedly, the disclosure encompasses plants, plant parts, seeds, and tissue cultures of the commercially elite or elite *Thlaspi* variety.

The plant part may comprise a microspore, pollen, ovary, ovule, embryo sac, egg cell, cutting, root, stem, cell or protoplast. Additionally, the tissue culture may comprise regenerable cells or protoplasts, wherein the cells or protoplasts of the tissue culture are derived from a tissue comprising a leaf, pollen, embryo, cotyledon, hypocotyl, meristematic cell, root, root tip, anther, flower, seed or stem.

The disclosure also relates to the *Thlaspi* variety designated 182002-B-B-31, representative seed of *Thlaspi arvense* variety 182002-B-B-31 having been deposited under NCMA Accession Number 202210001.

As disclosed herein is an elite or commercially elite *Thlaspi* variety with reduced pod shattering, and/or early maturity, the variety having an ancestor thereof that is the cultivar of 2032, representative seed of which has been deposited under NCMA Accession Number 202210002. In an embodiment, the trait is reduced seed pod shattering, early maturity, or a combination thereof. The disclosure also encompasses plants and plant parts of the elite or commercially elite variety having 2032 as an ancestor. The plant part may comprise a microspore, pollen, ovary, ovule, embryo sac, egg cell, cutting, root, stem, cell, protoplast, or tissue culture of regenerable cells or protoplasts. In an embodiment, the cells or protoplasts of the tissue culture are derived from a tissue comprising a leaf, pollen, embryo, cotyledon, hypocotyl, meristematic cell, root, root tip, anther, flower, seed or stem.

Shatter Resistance

The Brassicaceae plants and plant materials described herein having reduced seed pod shatter can be used as a cover crop that reduces nutrient leaching and soil erosion while also having commercial and industrial uses such that the plants produce an economically viable product such as an edible oil, edible meal, and/or oil that can be used for the production of biodiesel, jet fuel, and/or other bioproducts, medicinal product, food product, or the like.

The shatter resistant plants and plant materials described herein can be derived from any suitable species within the Brassicaceae family. An oilseed plant can be a member of the family Brassicaceae (e.g., the mustard family). For example, a plant can be a member of the genus *Thlaspi*. Examples of plants include, without limitation, pennycress, rapeseed, soybean, sunflower, canola, flax, camelina, *Carinata, Lepidium*, and *Crambe* plants. In some cases, a domesticated oilseed plant having reduced seedpod shatter as described herein can be a pennycress plant.

Preferably, the plants and plant materials provided herein have a reduced seedpod shatter trait, meaning a greater amount of force is required to break open the seedpods of the plants described herein than the amount of force needed to break open a wild type seedpod. It will be appreciated that comparable oilseed plants are used when determining whether or not a particular oilseed plant has reduced seedpod shatter. Reduced seedpod shatter can also be referred to as, for example, increased pod shatter resistance. For example, a seedpod of a wild type pennycress plant typically shatters under about 3 grams to about 20 grams of force (e.g., pulling force). In some cases, a pennycress plant having reduced seedpod shatter as described herein can have seedpods that require greater than about 10 (e.g., greater than about 20, greater than about 30, greater than about 40, greater than about 50, greater than about 60, greater than about 70, greater than about 80, greater than about 90, greater than about 100, greater than about 110, or greater than about 120) grams force (e.g., pulling force) to shatter. In some cases, an oilseed plant having reduced seedpod shatter as described herein can have seedpods that require about 20 grams to about 120 grams (e.g., about 20 grams to about 100 grams, about 20 grams to about 90 grams, about 20 grams to about 80 grams, about 20 grams to about 60 grams, about 20 grams to about 45 grams, about 25 grams to about 120 grams, about 30 grams to about 120 grams, about 40 grams to about 120 grams, about 50 grams to about 120 grams, about 70 grams to about 120 grams, about 100 grams to about 120 grams, about 25 grams to about 100 grams, about 30 grams to about 90 grams, about 40 grams to about 80 grams, or about 50 grams to about 70 grams) force (e.g., pulling force) to shatter. For example, a pennycress plant having reduced seedpod shatter as described herein can have seedpods that require about 20 grams to about 45 grams pulling force to shatter.

For example, a pennycress plant having reduced seedpod shatter as described herein can have seedpods that require about 40 grams to about 120 grams pulling force to shatter. In some cases, an oilseed plant having reduced seedpod shatter as described herein can have seedpods that are resistant to shatter under about 10 grams to about 30 grams pulling force. For example, a pennycress plant having reduced seedpod shatter as described herein can have seedpods that are resistant to shatter under less than about 30 (e.g., less than about 25, less than about 20, less than about 18, less than about 15, less than about 12, less than about 10, or less than about 7) grams force (e.g., pulling force). The oilseed plants having reduced seedpod shatter as described herein can be identified by, for example, measuring shatter resistance (e.g., as described in the Examples).

The plants and plant materials having the reduced seedpod shatter trait and/or early maturity trait as described herein can be from the 2032 cultivar or the 182002-B-B-31 variety, or progeny/varieties derived from those lines.

As described herein, the Brassicaceae plants and plant materials having the reduced seedpod shatter trait can include any appropriate type of modification(s) in one or more genes that encode polypeptides involved in seedpod shatter. For example, a modification can be a loss-of-function modification. As used herein, a loss-of-function modification can be any modification that is effective to reduce polypeptide expression or polypeptide function. In some cases, reduced polypeptide expression or reduced polypeptide function can be eliminated polypeptide expression or eliminated polypeptide function. Examples of genetic modifications include, without limitation, deletions, insertions, substitutions, translocations, inversions, and duplications.

Brassicaceae plants and plant materials having the reduced seedpod shatter trait provided by the 2032 cultivar as described herein include one or more modification(s) in one or more genes that encode any appropriate polypeptide involved in seedpod shatter. Genes that encode polypeptides involved in seedpod shatter that are particularly relevant include the INDEHISCENT (IND) gene. In certain embodiments, the Brassicaceae plants and plant materials will comprise ind1-4 alleles found in *Thlaspi arvense* cultivar 2032 deposited under NCMA Accession Number 202210002. The ind1-4 allele is a recessive mutation in the IND gene which confers desirable reduced pod shatter characteristics while minimizing undesirable levels of reduced threshability associated with other recessive ind alleles (e.g., amorphic ind alleles with complete loss of IND gene function). Secondary genes of relevance include, without limitation, SPT, alcatraz (ALC), indehiscent (IND), replumless (RPL), shatterproof (SHP; e.g., SHP1 and SHP2), fruitfull (FUL), nac secondary wall thickening promoting factor1 and 3 (NST1 and NST3), pinoid (PID), and dz polygalacturonase 1 and 2 (ADPG1 and ADPG2). Polypeptides involved in seedpod shatter include, without limitation, SPT, ALC, IND, RPL, SHP (e.g., SHP1 and SHP2), FUL, NST1, NST3, PID, ADPG1, ADPG2 and the IND polypeptides.

Brassicaceae plants comprising the reduced seedpod shatter (RSS) trait phenotypes can be identified by a variety of techniques that distinguish plants with pod shatter resistance from plants which are prone to pod shatter (e.g., plants comprising a wild-type IND gene). In some embodiments, pod shatter in RSS plants and suitable controls (e.g., plants lacking an RSS trait or containing a wild-type IND gene) can be measured in controlled environments (e.g., growth chambers and/or greenhouses) or in field trails. Methods of measuring pod shatter include: (i) percent shattered pods determination by visual evaluation of plants (US20220298519, incorporated herein by reference in its entirety) where a reduction in the percent of shattered pods in comparison to a control indicates pod shatter resistance; and (ii) measurement of weight of seeds dropped per unit area under the plant pre-harvest and/or during harvest (US20190053458, incorporated herein by reference in its entirety). Methods of measuring pod shatter resistance also include: (i) methods which measure the effect of mechanical force on pod shatter (e.g., measurement of the effect of mechanical agitation for specific speeds and times on pod shatter as disclosed US20220298519, incorporated herein by reference in its entirety) where a reduction in the percent of shattered pods in comparison to a control indicates pod shatter resistance; and (ii) measurement of the amount of force required to cause pod opening (e.g., use of a gram force meter to measure force needed to break open a pod US 2019/0053458, incorporated herein by reference in its entirety) where an increase in the amount of force required is indicative of pod shatter resistance. In certain embodiments, a gram force tension gauge (SSEYL ATG-100-2 Tension Gauge) attached to a two-inch alligator clip can be used to determine the force required to break apart seedpods at the septum, where one side of a pennycress pod can be clipped and the other side can be pulled manually until the pod breaks apart. Another method is to subject plants to a consistent level of force and then to evaluate/measure the percent of pod shatter. In certain embodiments, seed pods can be pressed through a set of rollers and shattering of the seed pods evaluated/measured (e.g., by determining the percent of pod shatter) following the stress).

Brassicaceae plants, plant parts, seeds, and seed lots comprising the aforementioned or otherwise disclosed RSS trait and/or EM trait are also provided herein. In certain embodiments, seed lots comprising a population of Brassicaceae plant seed comprising untreated or treated Brassicaceae seed are provided. Such populations of seed in the seed lots can comprise at least 70%, 80%, 90%, 95%, 96%, 97%, 98%, 99%, or 100% *Brassica* plant seed comprising the RSS and/or EM trait. A seed lot can comprise at least 1, 2, 5, 10, 20, 50, 100, 500, or 1,000 kg of seed. Use of any of the aforementioned treated or untreated Brassicaceae plant seed lots to make animal feed (e.g., livestock or poultry feed), non-defatted Brassicaceae. seed meal, or defatted Brassicaceae seed meal is also provided. Use of any of the aforementioned Brassicaceae seed lots to provide whole, cracked or rolled seed to animals (e.g., poultry) in scratch grain is also provided.

It is to be understood that while certain embodiments have been described in conjunction with the detailed description thereof and examples, the foregoing and following description is intended to illustrate and not limit the scope of the disclosure. Other aspects, advantages, and modifications are within the scope of the following embodiments and claims.

Seed Traits

Although a variety of characteristics distinguish the 2032 cultivar, black seed color and wild-type seed fiber content are examples of traits of the 2032 cultivar.

Pennycress has value in both its oil and the resulting meal following the removal of oil. The meal is used for animal feed and is typically valued for its starch and protein. High seed fiber content reduces animal feed value as fiber is non-digestible. Fiber is measured by multiple measures including Crude Fiber (CF), Acid detergent Fiber (ADF) and Neutral detergent fiber (NDF). ADF is a useful determinant in estimating the energy available to animals. In certain embodiments, ADF can be measured gravimetrically using Association of Official Analytical Chemists (AOAC) Official Method 973.18 (1996): "Fiber (Acid Detergent) and Lignin in Animal Feed". In certain embodiments, modifications of this method can include use of Sea Sand for filter aid as needed. NDF can be determined as disclosed in JAOAC 56, 1352-1356, 1973. In certain embodiments, fiber (ADF and/or NDF), protein, and/or oil content can be determined by Near-infrared (NIR) spectroscopy.

In certain embodiments, the varieties and elite plants and plant materials described herein which comprise the reduced seedpod shatter and/or early maturity traits of 2032 cultivar have decreased fiber content as compared to the corresponding wild type plants or 2032 cultivar. Typically, the level of acid detergent fiber (ADF) in wild type pennycress seed varies from about 25% to about 31% by dry weight. In some embodiments, the varieties and elite plants and plant materials described herein can have seeds with an ADF content of 20% or less by dry weight by dry weight. Such seeds with an ADF content of 20% or less will typically be yellow or brown in color rather than black. U.S. Pat. No. 10,709,151, incorporated herein by reference in its entirety, describes *Thlaspi* sp. plants having reduced seed coat fiber and lighter-colored seed coat due to reduced proanthocyanidin content, increased protein content, and/or higher seed oil content and methods of making such plants. Polypeptides affecting seed fiber content include, without limitation, TRANSPARENT TESTA1 (TT1) through TRANSPARENT TESTA19 (TT19) (e.g., TT1, TT2, TT3, TT4, TT5, TT6, TT7, TT8, TT9, TT10, TT12, TT13, TT15, TT16, TT18, and TT19), TRANSPARENT TESTA GLABRA1 and 2 (TTG1 and TTG2), GLABROUS 2 (GL2), GLABROUS 3 (GL3), ANR-BAN, and AUTOINHIBITED H+-ATPASE 10 (AHA10). Varieties and elite plants and plant materials described herein which comprise the reduced seedpod shatter and/or early maturity traits of 2032 cultivar and either loss-of-function mutations in genes encoding one or more of the aforementioned polypeptides or transgenes which suppress expression of those genes are thus provided.

In certain embodiments, the varieties and elite plants and plant materials described herein which comprise the reduced seedpod shatter and/or early maturity traits of 2032 cultivar have decreased seed glucosinolate content as compared to the 2032 cultivar. U.S. Pat. No. 10,988,772, incorporated herein by reference in its entirety, discloses describes *Thlaspi* sp. plants having reduced sinigrin content which can comprise one or more loss-of-function mutations in one or more genes that encode polypeptides involved in glucosinolate biosynthesis, in glucosinolate transport, in glucosinolate hydrolysis, regulating expression of genes encoding glucosinolate biosynthetic and/or transport genes (e.g., transcription factors) or can comprise transgenes or genome rearrangements that suppress expression of those biosynthetic, transporter, hydrolysis, or expression regulator (e.g., transcription factor) encoding genes. Polypeptides affecting these traits include, without limitation, AOP2, BCAT4, BCAT6, $CYP79F_1$, CYP83A1, GTR1, GTR2, MYB28 (HAGI), MYB29, MYB76, TFP, BHLH05, IMD1, CYP79B3, MAM1, FMO-GS-Oxl, and UGT74B-1 polypeptides. Varieties and elite plants and plant materials described herein which comprise the reduced seedpod shatter and/or early maturity traits of 2032 cultivar and either loss-of-function mutations in genes encoding one or more of the aforementioned polypeptides or transgenes which suppress expression of those genes are thus provided.

In certain embodiments, the varieties and elite plants and plant materials described herein which comprise the reduced seedpod shatter and/or early maturity traits of 2032 cultivar have decreased seed erucic acid content as compared to the 2032 cultivar. U.S. patent Ser. No. 11/396,657, incorporated herein by reference in its entirety, discloses describes *Thlaspi* sp. plants having reduced erucic acid content which can comprise one or more loss-of-function mutations in the FAE1 gene. Varieties and elite plants and plant materials described herein which comprise the reduced pod shatter and/or early maturity traits of 2032 cultivar and either loss-of-function mutations in the FAE1 gene or transgenes which suppress expression of the FAE1 genes are thus provided. In certain embodiments, varieties and elite plants and plant materials described herein which comprise the reduced seedpod shatter and/or early maturity traits of 2032 cultivar can have seed containing oil comprising less than 5% erucic acid by weight or less than 2% erucic acid by weight.

Early Maturation

An important consideration in the use and selection of a cover crop is termination timing. Cover crops are generally planted to reduce soil erosion and to improve overall soil quality in preparation for the next planting season. The timing of termination of the cover crop is significant, as cover crops must be removed from a field before the follow-on primary summer crop may be planted, such as corn or soybean. Farmer income is typically driven by performance of the primary crop and adoption of cover crops is enhanced when they do not negatively impact primary crop performance by delaying planting.

*Thlaspi arvense*, for example, is typically planted anytime between the end of August through the third week in October in the U.S. Midwest region. Harvesting generally occurs between mid-May and early June. Globally, *Thlaspi arvense* can be planted in any crop rotation that enables early fall seeding producing at least a 2.5-3.5 centimeter rosette prior to the end of the fall growing season, and harvest timing which allows for a summer crop appropriate for the geography to be planted directly after harvest. Crop rotations which lend themselves to the use of *Thlaspi arvense* as a cover crop include but are not limited to summer crops of corn followed by soy, soy followed by corn. In some regions where a winter wheat crop might be followed by double-crop soy, *Thlaspi arvense* might be grown as an alternative to winter wheat as *Thlaspi arvense* matures two to three weeks earlier than winter wheat thus enabling a longer growing season for the following soy crop. In general *Thlaspi arvense* may be used in similar crop rotations between 35 degrees and 45 degrees latitude in both the northern and southern hemispheres in which summer crops are planted in the spring and harvested in the fall. At the stage where the seed pods of *Thlaspi arvense* are filled and maturing, they will begin to yellow and transition to tan/brown. The seed pods are considered fully matured when they achieve a dry, brown state. Once pods across the entire plant are dried down, the seeds can be harvested. The Brassicaceae varieties, and particular *Thlaspi arvense* varieties described herein beneficially demonstrate sufficiently early maturation to enable harvest between early and late-May in the US lower Midwest ranging to late-May to mid-June in the US upper midwest allowing dispersal of residue onto the soil and enabling planting of a summer crop directly into the residue.

*Thlaspi arvense* Cultivar 2032 and 2032:WG:B28874A_EDIT

The 2032 cultivar originated from a wild-collected parent. In brief, a population of wild collected seed was sowed, and plants showing early maturity and seedpod shatter resistance traits were selected from the population. A line confirming these two agronomic traits was propagated and designated as the 2032 cultivar. The wild accession 2032 has several defining characteristics, some of which are of a positive nature and some which are negative. Two of the key positive characteristics are general early maturity (e.g., "earliness"), which manifests most importantly as the ability to harvest 2032 as much as a week before virtually all other North American collected winter pennycress sources, and resistance to shattering, which protects against yield loss at harvest time when weather or operational factors delay harvest past an ideal date. The 2032 cultivar also has acceptable yield levels for a wild accession. Accession 2032 is thus useful in pennycress breeding programs as a donor of desirable earliness, shatter resistance, and yield potential traits. The levels of earliness and shatter resistance exhibited by 2032 have not been found in an original pennycress germplasm collection comprising nearly 900 accessions. Among the key negative characteristics of 2032 is a propensity to lodge prior to harvest, which renders harvest difficult and can lead to yield loss and reduced grain quality. The 2032 seed also has high levels of seed glucosinolates (sinigrin), seed fiber (as evidenced by dark seed color), and erucic acid which are characteristic of wild, undomesticated pennycress accessions and undesirable (U.S. Pat. Nos. 10,709,151; 1,139,657; and 11685927; each incorporated herein by reference in its entirety; Sedbrook et al. Plant Sci. 2014, 227:122-32. doi: 10.1016/j.plantsci.2014.07.008). The level of lodging exhibited by 2032 also renders it unacceptable as a commercial product. A description of the 2032 cultivar is provided in Table 1.

A description of 2032:WG:B28874A_EDIT, a gene edited plant derived from the 2032 cultivar having reduced seed fiber content as well as modified seed color and reduced erucic acid content is also provided in Table 1. Gene editing of 2032 plants and selfing of edited plants were used to obtain 2032:WG:B28874A_EDIT plants. 2032:WG:B28874A_EDIT which are homozygous for loss-of-function mutations: (i) in the endogenous pennycress TT8 gene which confer reduced seed coat fiber content and lighter-colored seed coat traits essentially as disclosed in U.S. Pat. No. 10,709,151, which is hereby incorporated by reference in its entirety; and (ii) in the FAE1 gene which confer reduced erucic acid content in seeds essentially as described in U.S. Pat. No. 11,396,657, which is hereby incorporated by reference in its entirety.

TABLE 1

| PLANT | 2032 | 2032:WG:B28874A_EDIT |
|---|---|---|
| Plant Height (cm) | 49.09 | 49.41 |
| STEM | | |
| Stem Diameter (mm) | 6.11 | 5.45 |
| Stem Anthocyanin | Weak (1.70) | Weak (2.00) |
| LEAVES | | |
| Leaf Color | Light Green (1.0) | Light Green (1.10) |
| Leaf Margin Serration | Weak (1.10) | Weak (1.50) |
| FLOWERS | | |
| Flower Maturity Class | Early (1.60) | Very Early (1.30) |
| PODS | | |
| Seeds Per Pod | 10.84 | 10.38 |
| Pedicel Length (mm) | 8.83 | 8.46 |
| SEED | | |
| Seed Color | Black | Yellow |
| 1000 Seed Weight (g) | 1.47 | 1.46 |
| GRAIN QUALITY | | |
| Oil % | 29.27 | 29.67 |
| Erucic acid % of total oil | 29.76 | 1.75 |
| Protein % | 33.43 | 34.18 |
| Sinigrin Content (µmol per g) | 121.61 | 125.24 |

*Thlaspi arvense* Variety 182002-B-B-31

The 182002-B-B-31 variety is derived from the 2032 cultivar and has the pedigree 2032//1120/1157-B-9)B-B-31. The pedigree of this variety and other varieties disclosed here is disclosed as follows. A slash indicates a cross between two lines. One slash indicates the first cross in a series of crossing and two slashes indicate the second cross in the series. The ")" separates the crossing structure from the selfing (or other) family structure. Dashes indicate selfing and letters or numbers following dashes indicate specific family structure for specific generations. "B" indicates that seed was bulked (most commonly a balanced bulk across selfed individuals within the generation). A number indicates that a specific plant was retained within that generation for subsequent evaluation. The ")" in the pedigree of 182002-B-B-31 separates the pedigree from lineage. The B not preceded by a "-" indicates the bulk $F_2$. Each subsequent dash indicates a generation of selfing with specific actions noted by a "B" indicating a bulk without selection or a number indicating selection of a specific plant. Thus, 182002-B-B-31 is an $F_4$ derived line as subsequent generations were all bulked.

Stepping back a generation, the pedigree nomenclature in the case of 1120/1157-B-9 is similar although the $F_1$ cross between parents indicated by the slash was not separated from the family structure with a ")". In this case the first dash indicates that the $F_1$ plants were self-pollinated, and the resulting $F_2$ was bulked "B". That bulk was then planted and self-pollinated (the second dash) and the $9^{th}$ plant was individually identified.

A description of the 182002-B-B-31 variety is provided in Table 2.

TABLE 2

| PLANT | |
|---|---|
| Plant Height (cm) | 57.22 |
| STEM | |
| Stem Diameter (mm) | 6.14 |
| Stem Anthocyanin | Weak (1.90) |
| LEAVES | |
| Leaf Color | Medium Green (2.00) |
| Leaf Margin Serration | Strong (3.00) |
| FLOWERS | |
| Flower Maturity Class | Late (4.7) |
| PODS | |
| Seeds Per Pod | 9.66 |
| Pedicel Length (mm) | 8.44 |
| SEED | |
| Seed Color | Black |
| 1000 Seed Weight (g) | 1.25 |
| GRAIN QUALITY | |
| Oil % | 28.65 |
| Erucic acid % of total oil | 32.04 |
| Protein % | 32.58 |
| Sinigrin Content (μmol per g) | 122.69 |

Table 3 provides a description of 182002-B-B-31:WG:B51774A:1, a gene edited plant of the 182002-B-B-31 variety having reduced seed fiber content as well as yellow seed color and reduced seed erucic acid content.

TABLE 3

| PLANT | 182002-B-B-31:WG:B51774A:1 |
|---|---|
| Plant Height (cm) | 57.97 |
| STEM | |
| Stem Diameter (mm) | 6.57 |
| Stem Anthocyanin | Medium (2.60) |
| LEAVES | |
| Leaf Color | Medium Green (2.20) |
| Leaf Margin Serration | Strong (3.00) |
| FLOWERS | |
| Flower Maturity Class | Medium Late (3.90) |
| PODS | |
| Seeds Per Pod | 8.59 |
| Pedicel Length (mm) | 7.30 |
| SEED | |
| Seed Color | Yellow |
| 1000 Seed Weight (g) | 1.21 |
| GRAIN QUALITY | |
| Oil % | 28.17 |
| Erucic acid % of total oil | 2.96 |
| Protein % | 33.76 |
| Sinigrin Content (μmol per g) | 128.62 |

Tables 4, 5, 6, and 7 show results from a spring 2023 greenhouse data collection. The results provide a comparison of pennycress cultivar 2032, 2032:WG:B28874A_EDIT, variety 182002_B-B-31, 182002-B-B-31:WG:B51774A:1, Fall_2015_53-B3-9 (a wild parent of 182002_B-B-31), and wild type grandparents of 182002_B-B-31. Pennycress varieties B3 and B28 are also shown as checks. Table 6 provides a description of the traits listed.

TABLE 4

| | OILNIRARV | OILERUCIC | SINIGRIN | SEEDCOLOR | PROTEINPCT |
|---|---|---|---|---|---|
| B3 Check | 28.77 | 31.86 | 112.17 | Black | 30.74 |
| B28 Check | 28.87 | 32.46 | 115.29 | Black | 31.07 |
| 2032 | 29.27 | 29.76 | 121.61 | Black | 33.43 |
| 2032:WG:B28874A_EDIT | 29.67 | 1.75 | 125.24 | Yellow | 34.18 |
| 182002-B-B-31 | 28.65 | 32.04 | 122.69 | Black | 32.58 |
| 182002-B-B-31:WG:B51774A:1 | 28.17 | 2.96 | 128.62 | Yellow | 33.76 |
| Wild-type Grandparent A (1157 wild accession) | 30.44 | 35.65 | 111.96 | Black | 30.90 |
| Wild-type Parent (FALL_2015_53-B-9; 1120/1157-B-9) | 29.25 | 33.91 | 118.11 | Black | 31.55 |
| Wild-type Grandparent B (1120 wild accession) | 30.93 | 36.31 | 109.90 | Black | 30.99 |
| No. of Reps | 10 | 10 | 10 | | 10 |
| Grand Mean | 29.34 | 26.30 | 118.40 | | 32.13 |
| Error d.f. | 71.00 | 71.00 | 71.00 | | 71.00 |
| R-Square | 0.64 | 0.98 | 0.65 | | 0.87 |
| 2*Error | 0.83 | 1.97 | 5.16 | | 0.54 |
| Alpha level | 0.05 | 0.05 | 0.05 | | 0.05 |
| LSD | 0.83 | 1.96 | 5.14 | | 0.54 |
| SED | 0.42 | 0.98 | 2.58 | | 0.27 |
| C.V. | 3.17 | 8.37 | 4.87 | | 1.87 |
| Heritability | 0.44 | 0.97 | 0.54 | | 0.84 |
| Min. Mean | 28.17 | 1.75 | 109.90 | | 30.74 |
| Max. Mean | 30.93 | 36.31 | 128.62 | | 34.18 |
| Min. Plot | 25.3 | 0.0 | 99.8 | | 29.0 |
| Max. Plot | 32.0 | 40.9 | 140.2 | | 35.2 |
| Range | 2.76 | 34.56 | 18.72 | | 3.43 |
| Residual | 0.87 | 4.85 | 33.24 | | 0.36 |
| Method | ACB | ACB | ACB | | ACB |

TABLE 5

| | Leaf color rating | Leaf Color | Leaf Margin Serration Rating | Leaf Margin Serration |
|---|---|---|---|---|
| B3WT Check | 2.30 | Medium Green | 1.80 | Medium |
| B28WT Check | 2.30 | Medium Green | 1.60 | Medium |
| 2032 | 1.00 | Light Green | 1.10 | Weak |
| 2032:WG:B28874A__EDIT | 1.10 | Light Green | 1.50 | Weak |
| 182002-B-B-31 | 2.00 | Medium Green | 3.00 | Strong |
| 182002-B-B-31:WG:B51774A:1 | 2.20 | Medium Green | 3.00 | Strong |
| Wild-type Grandparent A (1157 wild accession) | 1.70 | Medium Green | 1.70 | Medium |
| Wild-type Parent (FALL__2015__53-B-9; 1120/1157-B-9) | 3.00 | Medium Dark Green | 1.00 | Weak |
| Wild-type Grandparent B (1120 wild accession) | 1.90 | Medium Green | 1.60 | Medium |
| No. of Reps | 10 | | 10 | |
| Grand Mean | 1.94 | | 1.81 | |
| Error d.f. | 71.00 | | 71.00 | |
| R-Square | 0.74 | | 0.80 | |
| 2*Error | 0.36 | | 0.35 | |
| Alpha level | 0.05 | | 0.05 | |
| LSD | 0.35 | | 0.35 | |
| SED | 0.18 | | 0.18 | |
| C.V. | 20.43 | | 21.73 | |
| Heritability | 0.70 | | 0.77 | |
| Min. Mean | 1.00 | | 1.00 | |
| Max. Mean | 3.00 | | 3.00 | |
| Min. Plot | 1.0 | | 1.0 | |
| Max. Plot | 3.0 | | 3.0 | |
| Range | 2.00 | | 2.00 | |
| Residual | 0.16 | | 0.15 | |
| Method | ACB | | ACB | |

TABLE 6

| | Pedicel Length | PLANTHGTCM | SEED1000 | Seeds Per Pod |
|---|---|---|---|---|
| B3WT Check | 8.53 | 59.94 | 1.07 | 12.72 |
| B28WT Check | 8.27 | 56.77 | 1.02 | 11.26 |
| 2032 | 8.83 | 49.09 | 1.47 | 10.84 |
| 2032:WG:B28874A__EDIT | 8.46 | 49.41 | 1.46 | 10.38 |
| 182002-B-B-31 | 8.44 | 57.22 | 1.25 | 9.66 |
| 182002-B-B-31:WG:B51774A:1 | 7.30 | 57.97 | 1.21 | 8.59 |
| Wild-type Grandparent A (1157 wild accession) | 10.27 | 66.42 | 1.08 | 11.74 |
| Wild-type Parent (FALL__2015__53-B-9; 1120/1157-B-9) | 8.80 | 60.68 | 1.11 | 11.40 |
| Wild-type Grandparent B (1120 wild accession) | 10.73 | 68.46 | 1.04 | 11.95 |
| No. of Reps | 10 | 10 | 10 | 10 |
| Grand Mean | 8.85 | 58.44 | 1.19 | 10.95 |
| Error d.f. | 69.00 | 71.00 | 71 | 71.00 |
| R-Square | 0.72 | 0.77 | 0.85 | 0.60 |
| 2*Error | 0.65 | 3.64 | 0.07 | 1.17 |
| Alpha level | 0.05 | 0.05 | 0.05 | 0.05 |
| LSD | 0.64 | 3.63 | 0.07 | 1.17 |
| SED | 0.32 | 1.82 | 0.04 | 0.59 |
| C.V. | 8.16 | 6.96 | 6.69 | 12.00 |
| Heritability | 0.67 | 0.71 | 0.82 | 0.45 |
| Min. Mean | 7.30 | 49.09 | 1.02 | 8.59 |
| Max. Mean | 10.73 | 68.46 | 1.47 | 12.72 |
| Min. Plot | 6.7 | 45.7 | 0.9 | 5.9 |
| Max. Plot | 12.0 | 72.4 | 1.6 | 14.4 |
| Range | 3.43 | 19.37 | 0.45 | 4.13 |
| Residual | 0.52 | 16.56 | 0.01 | 1.73 |
| Method | ACB | ACB | ACB | ACB |

TABLE 7

| | Stem anthocyanin rating | Stem anthocyanin | Stem Diameter | Flower Mat Class Rating | Flower Mat Class |
|---|---|---|---|---|---|
| B3WT Check | 1.40 | Weak | 7.15 | 2.30 | Early |
| B28WT Check | 1.40 | Weak | 6.72 | 1.50 | Early |
| 2032 | 1.70 | Weak | 6.11 | 1.60 | Early |
| 2032:WG:B28874A__EDIT | 2.00 | Weak | 5.45 | 1.30 | Very Early |
| 182002-B-B-31 | 1.90 | Weak | 6.14 | 4.70 | Late |
| 182002-B-B-31:WG:B51774A:1 | 2.60 | Medium | 6.57 | 3.90 | Medium Late |
| Wild-type Grandparent A (1157 wild accession) | 2.60 | Medium | 8.11 | 2.00 | Early |
| Wild-type Parent (FALL__2015__53-B-9; 1120/1157-B-9) | 1.40 | Weak | 7.11 | 1.90 | Early |
| Wild-type Grandparent B (1120 wild accession) | 2.90 | Medium | 8.00 | 2.20 | Early |
| No. of Reps | 10 | | 10 | 10 | |
| Grand Mean | 1.99 | | 6.82 | 2.38 | |
| Error d.f. | 70.00 | | 70.00 | 71.00 | |
| R-Square | 0.66 | | 0.53 | 0.76 | |
| 2*Error | 0.45 | | 0.82 | 0.65 | |
| Alpha level | 0.05 | | 0.05 | 0.05 | |
| LSD | 0.45 | | 0.82 | 0.65 | |
| SED | 0.23 | | 0.41 | 0.32 | |
| C.V. | 25.51 | | 13.41 | 30.45 | |
| Heritability | 0.55 | | 0.45 | 0.71 | |
| Min. Mean | 1.40 | | 5.45 | 1.30 | |
| Max. Mean | 2.90 | | 8.11 | 4.70 | |
| Min. Plot | 1.0 | | 4.9 | 1.0 | |
| Max. Plot | 4.0 | | 9.9 | 6.0 | |
| Range | 1.50 | | 2.66 | 3.40 | |
| Residual | 0.26 | | 0.84 | 0.52 | |
| Method | ACB | | ACB | ACB | |

TABLE 8

| Trait | Description |
|---|---|
| Flower Mat Class Rating | Maturity class: 1 = Very early, 2 = early, 3 = medium early, 4 = medium late, 5 = late, 6 = very late |
| Flowering Maturity Class | Verbal rendition of Flower Maturity class rating |
| Leaf color | Verbal rendition of leaf color at late rosette stage |
| Leaf color rating | Number associated with leaf color. 1 = Light Green, 2 = medium green, 3 = medium dark green, 4 = dark green |
| Leaf Margin Serration | Verbal rendition of depth of serrations on leaf margins in rosette stage |
| Leaf margin serration rating | Depth of serration of leaf margins in rosette stage: 1 = Weak, 2 = medium, 3 = strong |
| OILERUCIC | Erucic acid percent of total oil. Approximately 1 gram of mature seed was placed in an individual clear glass vial for NIR analysis. |
| OILNIRARV | Oil % as measured NIR. Approximately 1 gram of mature seed was placed in an individual clear glass vial for NIR analysis. |
| Pedicel Length | Pedicel length midway on the main flower stem in mm |
| PLANTHGTCM | Plant height (cm) at end of flowering |
| Pod Ripening Class | Maturity rating for pod ripening in the field |
| PROTEINPCT | Seed protein % via ARV NIR. Approximately 1 gram of mature seed was placed in an individual clear glass vial for NIR analysis. |
| SEED1000 | 1000 seed weight in grams |
| SEEDCOLOR | Seed color at harvest |
| Seeds Per Pod | Seeds per pod averaged over 5 pods taken from the main flower stem |
| SINIGRIN | Sinigrin in micromoles per gram as measured via NIR. Approximately 1 gram of mature seed was placed in an individual clear glass vial for NIR analysis |

TABLE 8-continued

| Trait | Description |
|---|---|
| Stem Anthocyanin | Verbal rendition of stem Anthocyanin during peak flowering |
| Stem anthocyanin rating | Level of stem anthocyanin: 1 = absent. 2 = weak, 3 = medium, 4 = strong |
| Stem Diameter | Stem diameter of main stem in mm |

Breeding Programs and Methods

The present disclosure relates to methods of using the cultivars and varieties described herein in a breeding program. A breeding program for a particular line is typically initiated by the initial selection and crossing of two or more parental lines, followed by repeated selfing and selection, ultimately resulting in the production of many unique genetic combinations. Many different genetic combinations can be generated via crossing, selfing, and mutagenesis. In each cycle of evaluation, the plant breeder selects the germplasm to advance to the next generation. This germplasm is grown under chosen geographical, climatic and soil conditions and further selections are then made during and at the end of the growing season. The characteristics of the varieties developed are incapable of prediction in advance. This unpredictability is because the selection occurs in unique environments, with no control at the DNA level (using conventional breeding procedures), and with millions of different possible genetic combinations being generated. A breeder of ordinary skill cannot predict in advance the final resulting varieties that are to be developed, except possibly in a very gross and general fashion. Even the same breeder is incapable of producing the same variety twice by using the same original parents and the same selection techniques. This unpredictability commonly results in the expenditure of large research monies and effort to develop a new and superior canola variety.

*Brassica*, including pennycress, breeding programs utilize techniques such as mass and recurrent selection, backcrossing, pedigree breeding and haploidy. For a general description of pennycress breeding and characterization, see Sedbrook et al., New approaches to facilitate rapid domestication of a wild plant to an oilseed crop: Example pennycress (*Thlaspi arvense* L.), PLANT SCI. (2014) 122-132, which is herein incorporated by reference in its entirety.

Recurrent selection is used to improve populations of either self- or cross-pollinating *Brassica*. Through recurrent selection, a genetically variable population of heterozygous individuals is created by intercrossing several different parents. The best plants are selected based on individual superiority, outstanding progeny, and/or excellent combining ability. The selected plants are intercrossed to produce a new population in which further cycles of selection are continued. Various recurrent selection techniques are used to improve quantitatively inherited traits controlled by numerous genes.

Breeding programs use backcross breeding to transfer genes for a simply inherited, highly heritable trait into another line that serves as the recurrent parent. The source of the trait to be transferred is called the donor parent. After the initial cross, individual plants possessing the desired trait of the donor parent are selected and are crossed (backcrossed) to the recurrent parent for several generations. The resulting plant is expected to have the attributes of the recurrent parent and the desirable trait transferred from the donor parent. This approach has been used for breeding disease resistant phenotypes of many plant species, and has been used to transfer low erucic acid and low glucosinolate content into lines and breeding populations of *Brassica*.

Pedigree breeding and recurrent selection breeding methods are used to develop varieties from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding, five or more generations of selfing and selection are practiced: $F_1$ to $F_2$; $F_2$ to $F_3$; $F_3$ to $F_4$; $F_4$ to $F_5$, etc. For example, two parents that are believed to possess favorable complementary traits are crossed to produce an $F_1$. An $F_2$ population is produced by selfing one or several $F_1$'s or by intercrossing two $F_{1S}$. Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new varieties or cultivars. Backcrossing may be used in conjunction with pedigree breeding; for example, a combination of backcrossing and pedigree breeding with recurrent selection has been used to incorporate blackleg resistance into certain varieties of *Thlaspi arvense*.

Plants that have been self-pollinated and selected for type for many generations become homozygous at almost all gene loci and produce a uniform population of true breeding progeny. If desired, double-haploid methods can also be used to extract homogeneous lines. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar/variety used commercially, such as $F_1$ hybrid variety or open pollinated variety. A true breeding homozygous line can also be used as a parental line (inbred line) in a commercial hybrid. If the line is being developed as an inbred for use in a hybrid, an appropriate pollination control system should be incorporated in the line. Suitability of an inbred line in a hybrid combination will depend upon the combining ability (general combining ability or specific combining ability) of the inbred.

Various breeding procedures are also utilized with these breeding and selection methods. The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, pennycress breeders commonly harvest one or more pods from each plant in a population and thresh them together to form a bulk. Part of the bulk is used to plant the next generation and part is put in reserve. The procedure has been referred to as modified single-seed descent or the pod-bulk technique. The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired, doubled-haploid methods can be used to extract homogeneous lines.

The production of doubled haploids can also be used for the development of inbreds in the breeding program. For pennycress, microspore culture technique may be used to produce haploid embryos. The haploid embryos are then regenerated on appropriate media as haploid plantlets, doubling chromosomes of which results in doubled haploid plants. This can be advantageous because the process omits the generations of selfing needed to obtain a homozygous plant from a heterozygous source.

The development of a pennycress hybrid in a pennycress plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in pennycress, the vigor of the lines decreases. Vigor is restored when two different inbred lines are crossed to produce the hybrid. A consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Methods of producing an elite *Thlaspi* plant variety comprising a reduced seedpod shatter trait and/or an early maturity trait comprise: (a) crossing a plant of *Thlaspi arvense* cultivar 2032, representative seed of *Thlaspi arvense* cultivar 2032 having been deposited under NCMA Accession Number 202210002 with a second *Thlaspi* plant from a wild line or an elite or elite commercial variety lacking the reduced seedpod shatter trait and/or early maturity trait, to create population of progeny plants, (b) selecting from the progeny plants a plant with a reduced seedpod shatter and/or early maturity, and (c) repeating steps a and b for a sufficient number of times so that an elite variety is created with reduced seedpod shatter and/or early maturity.

The 2032 cultivar or 182002-B-B-31 variety may also be used to produce a double cross hybrid or a three-way hybrid. A single cross hybrid is produced when two inbred varieties are crossed to produce the $F_1$ progeny. A double cross hybrid is produced from four inbred varieties crossed in pairs (A×B and C×D) and then the two $F_1$ hybrids are crossed again (A×B)×(C×D). A three-way cross hybrid is produced from three inbred varieties where two of the inbred varieties are crossed (A×B) and then the resulting $F_1$ hybrid is crossed with the third inbred variety (A×B)×C. In each case, pericarp tissue from the female parent will be a part of and protect the hybrid seed.

Another form of commercial hybrid production involves the use of a mixture of male sterile hybrid seed and male pollinator seed. When planted, the resulting male sterile hybrid plants are pollinated by the pollinator plants. This method can be used to produce grain with enhanced quality grain traits, such as high oil.

Pollination

Self-pollination is common for pennycress, although a very low percentage of flowers are cross pollinated by insects and/or wind pollination. Given the high rate of self-pollination, in many instances, self-pollination of parental varieties is controlled to enable hybrid development. As such, self-incompatible (SI), cytoplasmic male sterile (CMS) or nuclear male sterile (NMS) plants may be used as the female parent in order to develop new pennycress hybrid varieties in an efficient manner.

In one instance, production of $F_1$ hybrids includes crossing a CMS Brassicaceae female parent with a pollen-producing male Brassicaceae parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self-pollination of the $F_1$ generation to produce several subsequent generations ensures that a desired trait is heritable and stable and that a new variety has been isolated. Discussion of cytoplasmic male sterility in Brassicaceae crops is found in Yamagishi & Bhat, *Cytoplasmic Male Sterility in Brassicaceae Crops*, BREED. SCI. (2014) 64(1): 38-47, and Hoffman, et al., *Hand Emasculation and Induced Male Sterility to Improve Field Pennycress* (*Thlaspi arvense* L.) Breeding, which are herein incorporated by reference in their entireties.

Promising advanced breeding lines commonly are tested and compared to appropriate standards in environments representative of the commercial target area(s). The best lines are candidates for new elite or commercial lines; and those still deficient in a few traits may be used as parents to produce new populations for further selection. For most traits the true genotypic value may be masked by other confounding plant traits or environmental factors. One method for identifying a superior plant is to observe its performance relative to other experimental plants and to one or more widely grown standard varieties. If a single observation is inconclusive, replicated observations provide a better estimate of the genetic worth.

Proper testing should detect any major faults and establish the level of superiority or improvement over current varieties. In addition to showing superior performance, there must be a demand for a new variety that is compatible with industry standards or which creates a new market. The introduction of a new variety commonly will incur additional costs to the seed producer, the grower, the processor and the consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically. The entire planting, selection, and testing process can last between six and fifteen years from the time of the first cross. This time period is demonstrative of the extensive efforts and resources involved in new variety breeding programs.

Hybrid seed production in particular generally involves the inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field, there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, through either visual or molecular methods.

Methods of Producing a Variety with Breeding Material

The 182002-B-B-31 variety and 2032 cultivar described herein may function as a source of breeding material in a plant breeding program. The 182002-B-B-31 variety and 2032 cultivar described herein can also function as a source of germplasm for use in a breeding and/or gene-editing program which provides improved traits (e.g., reduced seed fiber content, reduced seed erucic acid content, and/or reduced seed sinigrin content, all in comparison to a wild-type check, a 182002-B-B-31 variety or progeny thereof check, or a 2032 cultivar check). To select and develop a superior variety, it is necessary to identify and select genetically unique individuals that occur in a segregating population. The segregating population is the result of a combination of crossover events plus the independent assortment of specific combinations of alleles at many gene loci that results in specific and unique genotypes. Advancement of the germplasm base as a whole permits the maintenance or improvement of traits such as fertility restoration, fatty acid profile modification, other nutritional enhancements, industrial enhancements, herbicide resistance, insect or pest resistance, resistance to bacterial, fungal, or viral disease, reduced seed fiber content, earlier maturity, modified seed color, increased or modified seed protein composition, increased or modified seed oil content or fatty acid composition, reduced seed glucosinolate (e.g., sinigrin) content, and shatter resistance, and yield enhancements. Locus conversions or other gene editing or breeding techniques may be used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of 2032 may be characterized as having essentially the same phenotypic traits as 2032. The traits used for comparison may be any of the traits described herein. Further, as described herein, molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

Methods of Obtaining Genetic Markers and Characterization

Phenotypic and Genotypic Characterization

Phenotypic characteristics most often are observed for traits associated with seed yield, seed oil content, seed protein content, fatty acid composition of oil, glucosinolate content of meal, growth habit, lodging resistance, plant height, shatter resistance, etc. A plant's genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Particular markers used for these purposes may include any type of marker and marker profile which provides a means of distinguishing varieties. A genetic marker profile can be used, for example, to identify plants of the same variety or related varieties or to determine or validate a pedigree. In addition to being used for identification of pennycress cultivar 2032 and its plant parts, the genetic marker profile is also useful in developing a locus conversion of 2032. Particularly useful markers and marker profiles characteristic of cultivar 2032 and progeny obtained therefrom (e.g., elite varieties) by breeding and/or gene editing include markers and marker profiles diagnostic for the presence of the ind1-4 allele.

Molecular markers can be identified using any suitable laboratory technique, including techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods. One use of molecular markers is Quantitative Trait Loci (QTL) mapping. QTL mapping is the use of markers which are known to be closely linked to alleles that have measurable effects on a quantitative trait. Selection in the breeding process is generally based upon the accumulation of markers linked to the positive effecting alleles and/or the elimination of the markers linked to the negative effecting alleles in the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS).

Molecular data from 2032 may be used in a plant breeding process. Nucleic acids may be isolated from a seed of 2032 or from a plant, plant part, or cell produced by growing a seed of 2032 or from a seed of 2032 with a locus conversion, or from a plant, plant part, or cell of 2032 with a locus conversion. One or more polymorphisms may be isolated from the nucleic acids. A plant having one or more of the identified polymorphisms may be selected and used in a plant breeding method to produce another plant. A marker system, such as one based on SNPs, can be highly informative in linkage analysis relative to other marker systems in that multiple alleles may be present.

Methods of Isolating Nucleic Acids

A method comprising isolating nucleic acids, such as DNA, from a plant, a plant part, plant cell or a seed of the pennycress varieties disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The nucleic acids isolated can comprise all, substantially all, or essentially all of the genetic complement of the plant. The nucleic acids isolated can comprise a genetic complement of the pennycress variety. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like.

Favorable genotypes and or marker profiles, optionally associated with a trait of interest, may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes. In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences).

Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme and expression methods. In some examples, no reference genome sequence is needed in order to complete the analysis. Cultivar 2032 or variety 182002-B-B-31 and its plant parts can be identified through a molecular marker profile. Such plant parts may be either diploid or haploid. Also encompassed and described are plants and plant parts substantially benefiting from the use of cultivar 2032 in their development, such as cultivar 2032 or variety 182002-B-B-31 comprising a locus conversion or single locus conversion.

Methods of Producing Progeny

The 2032 cultivar can be advantageously used in accordance with the breeding methods described herein to produce hybrids and other progeny plants retaining desired trait combinations of 2032. Disclosed are methods for producing a pennycress plant by crossing a first parent pennycress plant with a second parent pennycress plant wherein either the first or second parent pennycress plant is pennycress cultivar 2032. Further, both first and second parent pennycress plants can come from the pennycress cultivar 2032. Either the first or the second parent plant may be male sterile. Methods for producing subsequent generations of seed from seed of cultivar 2032, harvesting the subsequent generation of seed; and planting the subsequent generation of seed are provided.

Still further provided are methods for producing a 2032-derived pennycress plant by crossing pennycress cultivar 2032 with a second pennycress plant and growing the progeny seed, and repeating the crossing and growing steps with the pennycress 2032-derived plant from 1 to 2 times, 1 to 3 times, 1 to 4 times, or 1 to 10 times, inclusive of all integers within this range. Thus, any such methods using the pennycress cultivar 2032 are part of this disclosure, including for example, open pollination, selfing, backcrosses, hybrid production, crosses to populations, and the like. All plants produced using pennycress cultivar 2032 as a parent are within the scope of this disclosure, including plants derived from pennycress cultivar 2032. This includes pennycress lines derived from 2032 which include components for either male sterility or for restoration of fertility. Advantageously, the pennycress variety is used in crosses with other, different, pennycress plants to produce first generation ($F_1$) pennycress seeds and plants with superior characteristics.

Also provided is the use of the elite varieties described herein and plant parts thereof described in a breeding program. As used herein, the term plant includes plant protoplasts, plant cell tissue cultures from which pennycress plants can be regenerated, plant calli, plant clumps, and plant cells that are intact in plants or parts of plants, such as embryos, pollen, ovules, seeds, flowers, kernels, ears, cobs, leaves, husks, stalks, roots, root tips, anthers, silk and the like. The utility of pennycress cultivar 2032 also extends to crosses with other species. Commonly, suitable species include those of the family Brassicaceae, particularly other pennycress plants.

Gene Editing

The cultivars and varieties described herein may be developed using one or more gene editing techniques. Any suitable gene editing technique may be used.

Expression Vectors for Plant Transformation—Selectable Markers

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes

With transgenic plants according to the present disclosure, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a plant of the disclosure. In another embodiment, the biomass of interest is seed and/or fruit.

Likewise, by means of the present disclosure, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility.

In embodiments, the transgene encodes a non-translated RNA (e.g., RNAi) that is expressed to produce targeted inhibition of gene expression, thereby conferring the desired trait on the plant. In embodiments, the transgene encodes the machinery used for gene editing techniques. Any transgene, including those exemplified above, can be introduced into the plants of the disclosure through a variety of means including, but not limited to, transformation (e.g., genetic engineering techniques), conventional breeding, and introgression methods to introduce the transgene into other genetic backgrounds.

Plant Transformation

The advent of new molecular biological techniques has allowed the isolation and characterization of genetic elements with specific functions, such as encoding specific protein products. Any DNA sequences, whether from a different species or from the same species that are inserted into the genome using transformation are referred to herein collectively as "transgenes." Transformed versions of the claimed pennycress cultivar 2032 are provided in which transgenes are inserted, introgressed or achieved through genetic modification of native sequences.

Numerous methods for plant transformation have been developed, including biological and physical plant transformation protocols. See, for example, Rani et al., *Genetic Transformation in Oilseed Brassicas-A Review* INDIAN J. AGRICUL. SCI. (2013), 83(4): 367-373 and McGinn et al., *Molecular Tools Enabling Pennycress (Thlaspi Arvense) as a Model Plant and Oilseed Cash Cover Crop*, PLANT BIO-TECHNOL. J. (2019), 17(4): 776-788, both of which are herein incorporated by reference in their entireties. In addition, expression vectors and in vitro culture methods for plant cell or tissue transformation and regeneration of plants are available. See, for example, Gruber & Crosby, *Vectors for Plant Transformation* in METHODS IN PLANT MOLECULAR BIOL-OGY AND BIOTECHNOLOGY (Glick & Thompson, Ed.) (1993), 89-119, which is herein incorporated by reference in its entirety.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes as described in WO 2009/114321, which is herein incorporated by reference in its entirety. Another site-directed engineering method is through the use of zinc finger domain recognition (e.g., artificial zinc finger nucleases), transcription activator-like (TAL) effector-DNA modifying enzyme (TALE or TALEN), site-specific modifications performed through use of a CRISPR/Cas system, expression vectors, and the like. Further discussion of such techniques is found in U.S. Pat. Nos. 10,709,151 and 11,224,237, both of which are herein incorporated by reference in their entireties.

One or more traits which may be modified or introduced in the plants and methods disclosed herein include male sterility, herbicide resistance, insect resistance, pest resistance, modified fatty acid metabolism, modified carbohydrate metabolism, modified seed yield, modified oil percent, modified protein percent, modified lodging resistance, modified seed fiber content, modified seed glucosinolate content, and modified resistance to bacterial disease, fungal disease or viral disease. A genetic trait that has been engineered or modified (e.g., by gene editing or mutagenesis) into a particular pennycress plant using transformation techniques could be moved into another line using traditional breeding techniques that are well known in the plant breeding arts. For example, a backcrossing approach could be used to move a transgene from a transformed pennycress plant to an elite inbred line and the resulting progeny would comprise a transgene. Also, if an inbred line was used for the transformation, then the transgenic plants could be crossed to a different line in order to produce a transgenic hybrid pennycress plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. Aforementioned and other traits can be introduced into the of a plant of *Thlaspi arvense* cultivar 2032, representative seed of *Thlaspi arvense* cultivar 2032 having been deposited under NCMA Accession Number 202210002, in a gene of a plant of *Thlaspi arvense* variety 182002-B-B-31, representative seed of *Thlaspi arvense* variety 182002-B-B-31 having been deposited under NCMA Accession Number 202210001, or in a gene of a progeny plant thereof by transformation, gene editing, or mutagenesis (e.g., TILLING).

With transformed plants according to the present discovery, a foreign or modified protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Franca-Oliveira et al., *A Review on the Extraction and Processing of Natural Source-Derived Proteins through Eco-Innovative Approaches*, PROCESSES (2021), 9(1626): 1-24, which is herein incorporated by reference in its entirety.

A genetic map can be generated via conventional Restriction Fragment Length Polymorphisms (RFLP), Polymerase Chain Reaction (PCR) analysis, Simple Sequence Repeats (SSR), Single Nucleotide Polymorphisms (SNPs), and/or Whole Genome Sequencing (WGS) which identifies the approximate chromosomal location of the integrated DNA molecule coding for the foreign protein. Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques. Example transgenes include but are not limited genes that confer resistance to pests or disease, genes that confer or contribute to an altered grain characteristics (such as altered fatty acids, altered phosphate content, altered carbohydrates, altered antioxidant content or composition, altered seed amino acid content or composition), genes that control pollination, seed production, or male sterility, genes that create a site for site specific DNA integration, genes that affect abiotic stress resistance, genes that affect plant growth, genes that impact agronomic traits such as yield, flowering, plant growth, plant structure, seed shape, seed size, shatter resistance, or a combination thereof.

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic line. The transgenic line can then be crossed with another (non-transgenic or transgenic) line in order to produce a new transgenic line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Targeting Induced Local Lesions in Genomes (TILLING)

Breeding schemes of the present application can include crosses with TILLING® plant cultivars. TILLING® is a method in molecular biology that allows directed identification of mutations in a specific gene. TILLING® was introduced in 2000, using the model plant *Arabidopsis thaliana*. TILLING® has since been used as a reverse genetics' method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. A "bubble" forms at the mismatch of the two DNA strands (the induced mutation in TILLING® or the natural mutation or SNP in EcoTILLING), which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Imes Centre (UK), focusing on *Brassica rapa*; Fred Hutchinson Cancer Research, focusing on *Arabidopsis*; Southern Illinois University (USA), focusing on Soybean; John Imes Centre (UK), focusing on Lotus and *Medicago*; and INRA (France), focusing on Pea and Tomato. More detailed description on methods and compositions on TILLING® can be found in U.S. Pat. No. 5,994,075, US 2004/0053236, WO 2005/055704, and WO 2005/048692, each of which is hereby incorporated by reference for all purposes.

Thus, in some embodiments, the breeding methods of the present disclosure include breeding with one or more TILLING plant lines with one or more identified mutations.

Locus Conversion

The disclosure also encompasses a locus conversion, including a single locus conversion. The elite varieties described herein may function as a genetic source of breeding material, permitting the introduction of a new locus or trait. Direct transformation, backcrossing, and/or marker assisted selection represent non-limiting examples of methods that can be used to accomplish such an introgression.

A single locus conversion occurs when DNA sequences are introduced or modified through traditional breeding techniques, such as backcrossing or through transformation. DNA sequences, whether naturally occurring, modified as disclosed herein, or transgenes, may be introduced using traditional breeding techniques. Desired traits transferred through this process include, but are not limited to, fertility restoration, fatty acid profile modification, other nutritional enhancements, industrial enhancements, herbicide resistance, insect or pest resistance, resistance to bacterial, fungal, or viral disease, reduced seed fiber content, earlier maturity, modified seed color, increased or modified seed protein composition, increased or modified seed oil content or fatty acid composition, reduced seed glucosinolate content, and shatter resistance, and yield enhancements. The trait of interest is transferred from the donor parent to the recurrent parent, in this case, the trait of early maturity and/or shatter resistance is transferred from the *Thlaspi* cultivar(s) described herein into elite Brassicaceae lines. Single-gene traits may result from the transfer of either a dominant allele or a recessive allele. Selection of progeny containing the trait of interest is done by direct selection for a trait associated with a dominant allele. Selection of progeny for a trait that is transferred via a recessive allele will require growing and selfing the first backcross to determine which plants carry the recessive alleles. Recessive traits may require additional progeny testing in successive backcross generations to determine the presence of the gene of interest.

A locus conversion of 2032 or 182002-B-B-31 may otherwise retain the genetic integrity of 2032 or 182002-B-B-31, respectively. Alternatively, where 2032 or 182002-B-B31 are used as a genetic source material for the early maturity and/or shatter resistance trait(s), the early maturity and/or shatter resistance trait(s) may be introduced into an elite Brassicaceae variety, such that the elite Brassicaceae variety incorporates these traits and otherwise retains its genetic integrity.

It should be understood that the pennycress cultivars and varieties disclosed herein, through routine manipulation by cytoplasmic genes, nuclear genes, or other factors, can be produced in a male-sterile or restorer form. The cultivar 2032 or variety 182002-B-B-31 or any of the elite varieties described herein can be manipulated to be male sterile by any of a number of methods known in the art, including by the use of mechanical methods, chemical methods, self-incompatibility (SI), cytoplasmic male sterility (CMS), or nuclear male sterility (NMS). The term "manipulated to be male sterile" refers to the use of any available techniques to produce a male sterile version of cultivar 2032 and variety 182002-B-B-31 or any of the elite varieties described herein. The male sterility may be either partial or complete male sterility. Also disclosed are seed and plants produced by the use of cultivar 2032 and variety 182002-B-B-31 or any of the elite varieties described herein. Cultivar 2032 and variety 182002-B-B-31 and/or any of the elite varieties described herein can further comprise a component for fertility restoration of a male sterile plant, such as an Rf restorer gene.

Tissue Culture

Further reproduction of Brassicaceae plants can occur by tissue culture and regeneration. Tissue culture of various tissues and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this disclosure is to provide cells which upon growth and differentiation produce Brassicaceae plants having desired characteristics of the Brassicaceae plant population. Optionally, Brassicaceae plants can be regenerated from the tissue culture of the disclosure comprising all or essentially all of the physiological and morphological characteristics of the Brassicaceae plant population.

Additional Breeding Methods

This disclosure is also directed to methods for producing a Brassicaceae plant by crossing a first parent Brassicaceae plant with a second parent Brassicaceae plant wherein the first or second parent Brassicaceae plant is a Brassicaceae plant of the population. Further, both first and second parent Brassicaceae can come from the Brassicaceae plants of the population. Thus, any of the following exemplary methods the Brassicaceae plants of the population are part of this disclosure: selfing, backcrosses, hybrid production, crosses to populations, double haploid production, and the like. All plants produced using a Brassicaceae plant of the population as at least one parent are within the scope of this disclosure, including those developed from Brassicaceae plants derived from the Brassicaceae plants of the population. Advantageously, a Brassicaceae plant of the population can be used in crosses with other, different, Brassicaceae plants to produce the first generation ($F_1$) Brassicaceae hybrid seeds and plants with desirable characteristics. The Brassicaceae plants of the disclosure can also be used for transformation where exogenous transgenes are introduced and expressed by the plants of the disclosure. Genetic variants created either through traditional breeding methods or through transformation of the cultivars of the disclosure by any of a number of protocols known to those of skill in the art are intended to be within the scope of this disclosure.

The following describes exemplary breeding methods that may be used with the Brassicaceae plant population in the development of further Brassicaceae plants. One such embodiment is a method for developing progeny Brassicaceae plants in a Brassicaceae plant breeding program comprising: obtaining a plant, or a part thereof, of the Brassicaceae plants of the population, utilizing the plant or plant part as a source of breeding material, and selecting a progeny plant with molecular markers in common with a Brassicaceae plant of the population and/or with some, all or essentially all of the morphological and/or physiological characteristics of the Brassicaceae plant population. In representative embodiments, the progeny plant has at least 1, 2, 3, 4, 5, 6, 7, 8, 9, 10 or more of the morphological and physiological characteristics of the Brassicaceae plants of the population, or even all of the morphological and physiological characteristics of the Brassicaceae plant population so that the progeny Brassicaceae plant is not significantly different for the traits than the Brassicaceae plants of the population, as determined at the 5% significance level when grown in the same environmental conditions; optionally, with the presence of one or more desired additional traits (e.g., fertility restoration, fatty acid profile modification, other nutritional enhancements, industrial enhancements, herbicide resistance, insect or pest resistance, resistance to bacterial, fungal, or viral disease, reduced seed fiber content, earlier maturity, modified seed color, increased or modified seed protein composition, increased or modified seed oil content or fatty acid composition, reduced seed glucosinolate content, and shatter resistance, yield enhancements, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of progeny plants, comprising crossing a Brassicaceae plant of the population with another Brassicaceae plant, thereby producing a population of Brassicaceae plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from the Brassicaceae plants of the population, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of the Brassicaceae plants of the population. One embodiment of this disclosure is the Brassicaceae plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from the Brassicaceae plants of the population, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. A plant of this population may be selected and repeatedly selfed or sibbed with a Brassicaceae plant resulting from these successive filial generations. Another approach is to make double haploid plants to achieve homozygosity.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the disclosure encompasses progeny Brassicaceae plants having a combination of at least 2, 3, 4, 5, 6, 7, 8, 9, 10 or more of the characteristics as described herein for the Brassicaceae plants of the population, so that the progeny Brassicaceae plant is not significantly different for the traits than the Brassicaceae plants of the population, as determined at the 5% significance level when grown in the same environmental conditions. Using techniques described herein and those known in the art, molecular markers may be used to identify the progeny plant as progeny of the Brassicaceae plants of the population. Mean trait values may be used to determine whether trait differences are significant, and optionally the traits are measured on plants grown under the same environmental conditions.

Progeny of the Brassicaceae plants of the population may also be characterized through their filial relationship with the Brassicaceae plants of the population, as for example, being within a certain number of breeding crosses of the Brassicaceae plants of the population. A breeding cross is a cross made to introduce new genetics into the progeny, and is distinguished from a cross, such as a self or a sib cross or a backcross to a Brassicaceae plant of the population as a recurrent parent, made to select among existing genetic alleles. The lower the number of breeding crosses in the pedigree, the closer the relationship between the Brassicaceae plants of the population and its progeny. For example, progeny produced by the methods described herein may be within 1, 2, 3, 4, 5 or more breeding crosses of the Brassicaceae plants of the population.

In representative embodiments, a Brassicaceae plant derived from the Brassicaceae plants of the population comprises cells comprising at least one set of chromosomes derived from the Brassicaceae plants of the population. In embodiments, the Brassicaceae plant or population of Brassicaceae plants derived from the Brassicaceae plants of the population comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles from the Brassicaceae plants of the population, e.g., at least about 6.25%, 12.5%, 25%, 30%3, 35%, 40%, 45%, 50%, 55%, 60%, 65%, 70%, 80%, 85%, 90%9, 95% 96%, 97%, 98% or 99% of the genetic complement of the Brassicaceae plants of the population, and optionally is the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the Brassicaceae plant derived from the Brassicaceae plants of the population is one, two, three, four, five or more breeding crosses removed from the Brassicaceae plants of the population.

In representative embodiments, a plant derived from the Brassicaceae plants of the population is a double haploid plant, a hybrid plant or an inbred plant.

In embodiments, a hybrid or derived plant from the Brassicaceae plants of the population comprises a desired added trait. In representative embodiments, a Brassicaceae plant derived from the Brassicaceae plants of the population comprises all of the morphological and physiological characteristics of the population. In embodiments, the Brassicaceae plant derived from the Brassicaceae plants of the population comprises essentially all of the morphological and physiological characteristics of the population, with the addition of a desired added trait such as improved shatter resistance and/or early maturation.

Methods of Producing and Using a Commodity Plant Product

The disclosure also provides for methods of producing a commodity plant product comprising obtaining a plant or plant part of any of the varieties described herein and producing a commodity plant product from the plant or plant part.

Processing the Commodity Plant Product

The commodity plant products described herein may undergo one or more processing steps. For example, processing of the seed harvested from the plants described herein can include one or more of cleaning to remove foreign material and debris such as seed pods from the harvested seed, conditioning, such as cooling and/or removal or addition of moisture to the seed, wet milling, dry milling and sifting.

Another example commodity processing step includes the treatment of seeds. Methods of treating a seed or applying a treatment to a seed comprise applying a composition to a seed as a coating or otherwise. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a slurry, a mist, or a soak. The composition to be used as a seed treatment can be a pesticide, fungicide, insecticide, or antimicrobial.

Industrial, Commercial, and Research Uses

The commodity plant products described herein have a wide variety of uses. The harvest plants can be used as livestock feed and/or as a cover crop. Additionally, the plant products can be utilized in the production of an edible vegetable oil or other food products in accordance with known techniques. Plants and plant parts described herein can also be processed to produce products such as biodiesel, plastics, protein isolates, adhesives and sealants.

One such example is the use of a Brassicaceae variety as in an animal feed. Brassicaceae seed oil may be extracted by a variety of techniques, such as by using a screw press. Following extraction, the crushed seeds and residual oil remains as a press-cake. The unprocessed press-cake may be used as, or incorporated into, an animal feed as a source of protein and other nutrients. In some cases, the press-cake may be heated. Such a heating step may be useful for *Thlaspi arvense* varieties, where it is desirable to deactivate the myrosinase in the press-cake.

The varieties described herein may also be commoditized and used as a model plant system. For example, *Thlaspi arvense* is a self-pollinating plant with a relatively small stature and a diploid genome similar to other model plants, such as *Arabidopsis thaliana*. Model plants and model plant systems are highly useful for genetic, biochemical, and physiological study.

However, some existing models are limited due by their lack of agronomic potential, which hinders the ability to address questions specific to crop engineering and field performance. The Brassicaceae varieties described can beneficially be used in a model system that allows the combination of basic and applied research, as experiments can be performed on Brassicaceae varieties that directly test and/or improve agronomic traits. Additionally, the larger cell and organ sizes of Brassicaceae varieties will help facilitate a variety of research including live-cell imaging, biochemical analyses, and omics studies.

A still further example is the use of the Brassicaceae varieties described herein in the production of a biofuel and/or "drop-in" biofuel. A biofuel is broadly understood as any fuel derive from biomass, and particularly a renewable source of biomass. Drop-in biofuels are defined as a liquid bio-hydrocarbons that are functionally equivalent to petroleum fuels and are fully compatible with existing petroleum infrastructure. Members of the Brassicaceae, particularly *Thlaspi arvense*, have the natural ability to produce a large volume of seeds high in oil and protein. The Brassicaceae varieties described herein are therefore well-suited to generate billions of liters of oil annual throughout temperature climates, without displacing traditional crops, which is a concern for soybean, palm, and sunflower oils. A biofuel can be produced by a method comprising extracting a seed oil from seeds of a Brassicaceae variety and reacting the seed oil with a monohydric alcohol in the presence of a catalyst, thereby releasing the mono alkyl esters of long chain fatty acids from their glycerol backbone. This process is referred to as transesterification. Preferably, the Brassicaceae variety is a descendent of the elite varieties described herein, wherein the trait of reduced oil viscosity is introduced into an elite variety having improved shatter resistance, as described herein. In some embodiments, this variety also has the trait of low or no erucic acid. The traits of low erucic acid and/or reduced oil viscosity combined with improved shatter resistance beneficially results in a variety with a very high yield of oils compatible for use as a biofuel.

Further discussion of example uses of Brassicaceae commodity plants is found in McGinn, Michaela, *Developing Pennycress (Thlaspi arvense) as a Biodiesel Feedstock Crop*

*and Plant Model System* (2018) available at ir.library.illinoistate.edu/etd/871, which is herein incorporated by reference in its entirety.

Deposit

A deposit of at least 625 seeds of each of *Thlaspi arvense* cultivar 2032 and *Thlaspi arvense* variety 182002-B-B-31 have been made with the Provasoli-Guillard National Center for Marine Algae and Microbiota (NCMA) at Bigelow Laboratory for Ocean Sciences at 60 Bigelow Drive, East Boothbay, Maine 04544. The seeds were deposited with the NCMA on Oct. 6, 2022 and were harvested from the CoverCress greenhouse at 1249 N. Warson Rd., St. Louis, Missouri 63132 prior to the filing date of this application. The *Thlaspi arvense* cultivar 2032 seeds have been given the Accession Number 202210002 by the NCMA as the International Depository Authority. The *Thlaspi arvense* variety 182002-B-B-31 seeds have been given the Accession Number 202210001 by the NCMA as the International Depository Authority. Access to each of these deposits will be available during the pendency of the application to the Commissioner of Patents and Trademarks and persons determined by the Commissioner to be entitled thereto upon request. Upon allowance of any claims in the application, the Applicant will make available to the public, pursuant to 37 C.F.R. § 1.808, sample(s) of the deposit of at least 625 seeds of *Thlaspi arvense* cultivar 2032 and *Thlaspi arvense* variety 182002-B-B-31 deposited with the NCMA. These deposits of seed of *Thlaspi arvense* cultivar 2032 and *Thlaspi arvense* variety 182002-B-B-31 will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant(s) do not waive any infringement of their rights granted under this patent or rights applicable to *Thlaspi arvense* cultivar 2032 or *Thlaspi arvense* variety 182002-B-B-31 under the Plant Variety Protection Act (7 USC 2321 et seq.).

Embodiments

1. A commercially elite or elite *Thlaspi* variety comprising a reduced seedpod shatter trait and/or early maturity trait of *Thlaspi arvense* cultivar 2032, representative seed of *Thlaspi arvense* cultivar 2032 having been deposited under NCMA Accession Number 202210002.

2. The variety of embodiment 1, wherein the variety lacks the black seed trait, high fiber seed trait, increased lodging trait and/or reduced yield trait of *Thlaspi arvense* cultivar 2032.

3. The variety of embodiment 1, wherein the trait is reduced seed pod shattering.

4. The variety of embodiment 1, wherein the trait is early maturity.

5. A plant of the variety of embodiment 1.

6. A part of the plant of embodiment 5, wherein the part comprises a microspore, pollen, ovary, ovule, embryo sac, egg cell, cutting, root, stem, cell or protoplast.

7. Seed of the plant of embodiment 5.

8. A tissue culture of regenerable cells or protoplasts from the plant of embodiment 5.

9. The tissue culture of embodiment 8, wherein the cells or protoplasts of the tissue culture are derived from a tissue comprising a leaf, pollen, embryo, cotyledon, hypocotyl, meristematic cell, root, root tip, anther, flower, seed or stem.

The variety of embodiment 2, wherein the variety is 182002-B-B-31, representative seed of *Thlaspi arvense* variety 182002-B-B-31 having been deposited under NCMA Accession Number 202210001.

11. A method for producing an elite *Thlaspi* plant variety comprising a reduced seedpod shatter trait and/or an early maturity trait, the method comprising:
(a) crossing a plant of *Thlaspi arvense* cultivar 2032, representative seed of *Thlaspi arvense* cultivar 2032 having been deposited under NCMA Accession Number 202210002 or a plant of *Thlaspi arvense* variety 182002-B-B-31, representative seed of *Thlaspi arvense* variety 182002-B-B-31 having been deposited under NCMA Accession Number 202210001, with a second *Thlaspi* plant from a wild cultivar, an elite variety, or an elite commercial variety lacking the reduced seedpod shatter trait and/or an early maturity trait, to create population of progeny plants;
(b) selecting from the progeny plants a plant with a reduced seedpod shatter and/or early maturity; and
(c) repeating steps (a) and (b) for a sufficient number of times so that an elite variety is created with the reduced seedpod shatter trait and/or early maturity trait.

12. The method of embodiment 11, wherein the trait is reduced seed pod shattering.

13. The method of embodiment 11, wherein the trait is early maturity.

14. A method of producing a *Thlaspi* variety with reduced seed pod shattering and/or early maturity comprising:
(a) obtaining: (i) a plant of *Thlaspi arvense* cultivar 2032, representative seed of *Thlaspi arvense* cultivar 2032 having been deposited under NCMA Accession Number 202210002 or (ii) a plant of *Thlaspi arvense* variety 182002-B-B-31, representative seed of *Thlaspi arvense* variety 182002-B-B-31 having been deposited under NCMA Accession Number 202210001; and
(b) using the same as a source of breeding material in a plant breeding program.

15. The method of embodiment 14, wherein the trait is reduced seed pod shattering.

16. The method of embodiment 14, wherein the trait is early maturity.

17. A commercially elite or elite *Thlaspi* variety with reduced pod shattering and/or early maturity, the variety having an ancestor thereof that is the cultivar 2032, representative seed of *Thlaspi arvense* cultivar 2032 having been deposited under NCMA Accession Number 202210002.

18. The variety of embodiment 17, wherein the trait is reduced seed pod shattering.

19. The variety of embodiment 17, method wherein the trait is early maturity.

20. A plant of the variety of embodiment 17.

21. A part of the plant of embodiment 17, wherein the part comprises a microspore, pollen, ovary, ovule, embryo sac, egg cell, cutting, root, stem, cell or protoplast.

22. A tissue culture of regenerable cells or protoplasts from the plant of embodiment 20.

23. The tissue culture of embodiment 22, wherein the cells or protoplasts of the tissue culture are derived from a tissue comprising a leaf, pollen, embryo, cotyledon, hypocotyl, meristematic cell, root, root tip, anther, flower, seed or stem.

24. A method for obtaining a genetic marker for the trait of reduced seed pod shattering and/or early maturity comprising;

(a) isolating nucleic acids from seed of Brassicaceae variety 2032, representative seed of the variety having been deposited under NCMA Accession Number 202210002 or from a seed of a plant of *Thlaspi arvense* variety 182002-B-B-31, representative seed of *Thlaspi arvense* variety 182002-B-B-31 having been deposited under NCMA Accession Number 202210001; and (b) identifying the genetic marker that is associated with the trait of reduced shatter and/or early maturity; optionally wherein the trait is reduced seed pod shattering and the genetic marker comprises a DNA polymorphism linked to an ind1-4 allele of the IND gene; optionally wherein the trait is reduced seed pod shattering and the genetic marker comprises a DNA polymorphism linked to an ind1-4 allele of the IND gene.

25. A method of introgressing the trait of reduced seed pod shattering and/or early maturity into a plant variety comprising: performing marker assisted selection with the genetic marker of embodiment 24; optionally wherein the trait is reduced seed pod shattering and the genetic marker comprises a DNA polymorphism linked to an ind1-4 allele of the IND gene.

26. A method for producing a progeny plant of Brassicaceae variety 2032 with reduced seed shatter and/or early maturity for use in a plant breeding program comprising:

(a) crossing: (i) a plant of Brassicaceae variety 2032, representative seed of the variety having been deposited under NCMA Accession Number 202210002, or (ii) a plant of *Thlaspi arvense* variety 182002-B-B-31, representative seed of *Thlaspi arvense* variety 182002-B-B-31 having been deposited under NCMA Accession Number 202210001, with itself or with another plant;

(b) harvesting the resultant seed;

(c) growing the seed to produce a progeny plant; and (d) selecting a progeny plant with the trait of reduced seed shatter and/or early maturity.

27. A progeny plant produced by the method of embodiment 26, wherein the progeny plant has reduced seedpod shatter and/or early maturity as compared to a wild type Brassicaceae plant.

28. A seed produced by the method of embodiment 26.

29. A plant produced by growing the seed of embodiment 28.

30. A method for producing a Brassicaceae variety 2032-derived seed for use in a breeding program comprising:

(a) crossing: (i) a plant of Brassicaceae variety 2032, representative seed of the variety having been deposited under NCMA Accession Number 202210002, or (ii) a plant of *Thlaspi arvense* variety 182002-B-B-31, representative seed of *Thlaspi arvense* variety 182002-B-B-31 having been deposited under NCMA Accession Number 202210001, with itself or a second plant;

(b) harvesting seed therefrom and planting the seed to create a population of plants.

31. The method of embodiment 30, further comprising:

(c) crossing a plant grown from a Brassicaceae variety 2032-derived seed with itself or with a second plant to yield an additional Brassicaceae variety 2032-derived seed;

(d) growing the additional Brassicaceae variety 2032-derived seed of step (c) to yield an additional Brassicaceae variety 2032-derived plant;

(e) repeating the crossing and growing of steps (c) and (d) for an additional 1-10 generations to generate one or more further Brassicaceae variety 2032-derived plants; and (f) generating seed of the further Brassicaceae variety 2032-derived plants.

32. A method for developing a Brassicaceae variety in a Brassicaceae plant breeding program comprising;

applying plant breeding techniques comprising recurrent selection, backcrossing, pedigree breeding, marker enhanced selection, or transformation to the plant of embodiment 5, or its parts;

wherein the applying of the plant breeding techniques results in development of a Brassicaceae variety.

33. The method of embodiment 32, wherein the Brassicaceae variety is s a variety of a *Thlaspi* genus.

34. The method of embodiment 32, wherein the Brassicaceae variety is a variety of a *Thlaspi arvense* species.

35. A method of producing a commodity plant product comprising:

(a) obtaining the plant of embodiment 5, or a plant part thereof, and (b) producing the commodity plant product from the plant or plant part thereof, wherein the commodity plant product is an oil, biodegradable plastic, lubricant, biofuel, food or feed product, medicinal product, or a combination thereof.

36. A method for producing an elite *Thlaspi* plant variety comprising:

(a) introducing a loss-of-function mutation in a gene of a plant of *Thlaspi arvense* cultivar 2032, representative seed of *Thlaspi arvense* cultivar 2032 having been deposited under NCMA Accession Number 202210002, in a gene of a plant of *Thlaspi arvense* variety 182002-B-B-31, representative seed of *Thlaspi arvense* variety 182002-B-B-31 having been deposited under NCMA Accession Number 202210001, or in a gene of a progeny plant of *Thlaspi arvense* cultivar 2032 or *Thlaspi arvense* variety 182002-B-B-31 by gene editing or mutagenesis, wherein the plant exhibits the reduced seedpod shatter trait and/or early maturity trait the 2032 cultivar and the 182002-B-B-31 variety and wherein the mutation confers a trait which is absent from the 2032 cultivar, the 182002-B-B-31 variety, or progeny thereof, and (b) selecting for a progeny plant comprising the reduced seedpod shatter trait and/or the early maturity trait as well as the mutation which confers the reduced seed fiber content, reduced seed erucic acid content, and/or reduced seed sinigrin content trait.

37. The method of embodiment 36, wherein the trait which is absent from the 2032 cultivar or the 182002-B-B-31 variety is reduced seed fiber content, reduced seed erucic acid content, and/or reduced seed sinigrin content trait in comparison to seed fiber content, seed erucic acid content, and/or seed sinigrin content in a wild-type check, to a 182002-B-B-31 variety or progeny thereof check, or to a 2032 cultivar check.

38. The method of embodiment 37, wherein the mutation is a loss-of-function mutation which confers the reduced seed fiber content trait and the gene is the TT1, TT2, TT3, TT4, TT5, TT6, TT7, TT8, TT9, TT10, TT12, TT13, TT15, TT16, TT18, TT19, TTG1, TTG2, GL2, GL3, ANR-BAN, or AHA10 gene.

39. The method of embodiment 37, wherein the mutation is a loss-of-function mutation which confers the reduced seed sinigrin content trait and the gene is the MYB28, MYB29, MYB76, CYP83A1, AOP2, BCAT4, BCAT6, CYP79F$_1$, GTR1, GTR2, TFP, BHLH05, IMD1, CYP79B3, MAM1, FMO-GS-Oxl, or UGT74B1 gene.

40. The method of embodiment 37, wherein the mutation is a loss-of-function mutation which confers the reduced seed erucic acid content trait and the gene is the FAE1 gene.

EXAMPLES

Characteristics of *Thlaspi arvense* varieties are described below in Tables 10, 11, and 12. Tables 11 and 12 include the additional parental control of 1120/1157-B-9 as well as pennycress varieties B3 and B28 as commercial checks.

183006-B-13, 183002-B-9, 183002-B-6, and 183012-B-34 all have the 2032 cultivar as a parent and have the following pedigrees (using the nomenclature previously described):

183006-B-13=2032//1120/1136-B-58)B-13;

183002-B-9=2032//1036/1228-B-3)B-9, with 1036/1228-B-3 being the commercial pennycress variety B3

183002-B-6=2032//1036/1228-B-3)B-6, with 1036/1228-B-3 being the commercial pennycress variety B3

183012-B-34=2032//1120/1136-B-73)B-34

Thus, all of 183006-B-13, 183002-B-9, 183002-B-6, and 183012-B-34 are F$_3$ derived varieties. 183002-B-9 and 183002-B-6 are sister lines derived from the same breeding cross.

TABLE 10

| | | | | | | |
|---|---|---|---|---|---|---|
| | | | | 2020-2022 Field Trial Summary | | |
| | | | | Lines | | |
| Trait | 2032 | 182002-B-B-31 | 183006-B-13 | 183002-B-9 | 183002-B-6 | 183012-B-34 |
| Black Seed/High Fiber | hmz | hmz | hmz | hmz | hmz | hmz |
| Ind1-4 allele | hmz | hmz | hmz | Mixed | hmz | hmz |
| Shattering (% of pods dehisced at harvest) | Check | +22 ns | −3 ns | +5 ns | +5 ns | +4 ns |
| Harvest maturity rating (1 = Late, 5 = Early) | Check | −0.33 ns | +0.57** | −0.22 ns | +0.20 ns | +0.38* |
| Grain % Harvest Moisture | Check | −0.02 ns | +0.16 ns | +0.24 ns | −1.90*** | −034* |
| Lodging Rating Pre-Harvest (1 = Unharvestable, 5 = Erect) | Check | +1.30*** | +0.62*** | +0.44** | +0.64*** | −0.85*** |
| % Seed Oil Content | Check | −0.27** | −0.54** | −0.36** | −1.15*** | +2.24*** |
| Winter Stand Maintenance Rating (1 = Poor, 5 = Excellent) | Check | −0.35*** | +0.10 ns | +0.60*** | +0.18 ns | −0.50*** |
| Test Weight (pounds per bushel) | Check | −0.33 ns | +1.45 ns | −0.67** | −0.76*** | −0.69** |
| Grain Yield (pounds per acre) | Check | +396** | +17 ns | +55 ns | +42 ns | +59 | hmz indicates homozygous;
+indicates difference in desirable direction;
−indicates difference in undesirable direction;
ns indicates no significant difference (t-test);
*indicates t-test significant at alpha = 0.05;
**indicates t-test significant at alpha = 0.01;
***indicates t-test significant at alpha = 0.001

TABLE 11

| | | | | | | |
|---|---|---|---|---|---|---|
| | | | | 2020-2023 Field Trial Summary | | |
| | | | | Trait | | |
| Lines | Parentage | Black Seed/High fiber | ind1-4 allele | Shattering (% of Pods Dehisced at Harvest) | Harvest Maturity Rating (1 = Late, 5 = Early) | Harvest Maturity Date (days post April 30) |
| 2032 | 2032 | hmz | hmz | Check | Check | Check |
| 182002-B-B-31 | 2032//1120/1157-B-9 | hmz | hmz | 22 ns | −0.87*** | −1.67*** |
| | 1120/1157-B-9 | hmz | No | −13.83*** | −0.18 ns | NA |
| 183006-B-13 | 2032//1120/1136-B-58 | hmz | hmz | −3 ns | 0.22 ns | −0.04 ns |
| 183002-B-9 | 2032/B3 | hmz | Mixed | 5 ns | −0.09 ns | −0.47 ns |

TABLE 11-continued 2020-2023 Field Trial Summary

| | | Trait | | | | |
|---|---|---|---|---|---|---|
| Lines | Parentage | Black Seed/ High fiber | ind1-4 allele | Shattering (% of Pods Dehisced at Harvest) | Harvest Maturity Rating (1 = Late, 5 = Early) | Harvest Maturity Date (days post April 30) |
| 183002-B-6 | 2032/B3 | hmz | hmz | 5 ns | −0.24 ns | −1.59*** |
| 183012-B-34 | 2032//1120/1136-B-73 | hmz | hmz | 4 ns | 0.10 ns | 0.84** |
| B3 | 1036/1228 | hmz | No | −11.4** | −0.59*** | −1.89*** |
| B28 | 1228/1067 | hmz | No | −16.5* | −0.77* | −2.54*** | hmz indicates homozygous;

+indicates difference in desirable direction;

−indicates difference in undesirable direction;

ns indicates no significant difference (t-test);

* indicates t-test significant at alpha = 0.05;

**indicates t-test significant at alpha = 0.01;

***indicates t-test significant at alpha = 0.001

TABLE 12

| | | Trait | | | | | |
|---|---|---|---|---|---|---|---|
| Lines | Parentage | Grain % Harvest Moisture | Lodging Rating Pre-Harvest (1 = Unharvestable, 5 = Erect) | % Seed Oil Content | Winter Stand Maintenance Rating (1 = poor, 5 = Excellent) | Test Weight (lbs per bushel) | Grain Yield (lbs per acre) |
| 2032 | 2032 | Check | Check | Check | Check | Check | Check |
| 182002-B-B-31 | 2032//1120/1157-B-9 | −0.30 ns | 0.95*** | −1.08*** | 0.06 ns | −0.03 ns | 166** |
| | 1120/1157-B-9 | 0.00 ns | NA | −1.61*** | 0.38*** | NA | −192** |
| 183006-B-13 | 2032//1120/1136-B-58 | 0.09 ns | 0.73*** | −0.45*** | 0.25** | −1.47*** | 15 ns |
| 183002-B-9 | 2032/B3 | 0.23 ns | 0.63*** | −0.21 ns | 0.28*** | −0.86*** | 39 ns |
| 183002-B-6 | 2032/B3 | −1.23*** | 0.62*** | −1.01*** | 0.25** | −1.97*** | 20 ns |
| 183012-B-34 | 2032//1120/1136-B-73 | −0.06 ns | −0.43** | 1.33*** | −0.09 ns | −1.23*** | 18 ns |
| B3 | 1036/1228 | −1.10*** | 0.35*** | −0.60*** | −0.03 ns | −1.11*** | −41 ns |
| B28 | 1228/1067 | −1.22*** | 0.91*** | −0.74*** | −0.03 ns | −1.03*** | 92*** |

+indicates difference in desirable direction;

−indicates difference in undesirable direction;

ns indicates no significant difference (t-test);

* indicates t-test significant at alpha = 0.05;

**indicates t-test significant at alpha = 0.01;

***indicates t-test significant at alpha = 0.001

Comparisons shown in Table 13 demonstrate the clear differences between the 2032 and pennycress lines derived from standard North America wild type accessions. B28WT, B3WT and B73WT (checks) are all lines that resulted from the first generation of a product improvement breeding program. Each of these lines trace to a different original cross of wild accessions as defined in the Generation 1 Parental Pedigree column in Table 13. Table 13 presents data comparing 2032 to each of these three pre-commercial lines for the three key traits list above in addition to grain yield. 2032 clearly shows highly significantly improved shatter resistance, and earlier harvest maturity compared to the pre-commercial B28WT, B3WT and B73WT lines (checks). Conversely, 2032 shows highly significantly worse lodging resistance compared to these lines. 2032 has significantly lower yield than B28WT (a much later maturity line) and equal to slightly better yield than B3WT and B73WT.

TABLE 13

| | Breeding Generation 1 Parent (Check) | Generation 1 Parental Pedigree | Shattering[1] | Harvest Maturity[2] | Lodging[3] | Yield[4] |
|---|---|---|---|---|---|---|
| 2032 | B28WT | 1228/1067-B-28 | +16.5*** | +0.77*** | −0.91*** | −92*** |
| 2032 | B3WT | 1036/1228-B-3 | +11.4** | +0.59*** | −0.35*** | +41 ns |
| 2032 | B73WT | 1120/1136-B-73 | +14.6** | +0.60*** | −0.33*** | +89 * |

[1]Shattering (% of Pods Dehisced at Harvest) at locations demonstrating measurable shattering
[2]Harvest Maturity Rating (1 = Late, 5 = Early) across all locations
[3]Lodging Rating Pre-Harvest (1 = Unharvestable, 5 = Erect) at locations demonstrating measurable lodging
[4]Grain Yield (pounds per acre) across all locations
[5] B28WT and B3WT are commercial genotypes
+indicates difference in desirable direction;
−indicates difference in undesirable direction;
ns indicates no significant difference (t-test);
* indicates t-test significant at alpha = 0.05;
**indicates t-test significant at alpha = 0.01;
***indicates t-test significant at alpha = 0.001

A breeding program aimed at combining the earliness and shatter resistance offered by 2032 with the lodging resistance offered by the pre-commercial lines B28WT, B3WT and/or B73WT while maintaining or preferably enhancing the yield of the resulting progeny was undertaken. Table 14 presents examples of the results of that breeding program and provides comparisons between selected example genotypes (Breeding Generation 2 2032 Derived Line) in column 1 and their parents.

The results presented herein show that shattering resistance is largely qualitative and due to fixation of the recessive ind1-4 allele in the homozygous state. The genotypes for ind1-4 are presented in Table 14 for both the Gen2 Lines (all homozygous for ind1-4) and their parents (i.e., 2032 parents homozygous for ind1-4; B28WT, B3WT, and B73WT all carrying the wild-type IND1 allele). Although results reported in Table 14 are not statistically significant for shatter resistance, Gen2 Lines, all carrying ind1-4 are

TABLE 14

| Breeding Generation 2 2032 Derived line [Pedigree] (IND genotype)[6] | Parental control[5] [Pedigree] (IND genotype) | Deviations From Parental Control | | | |
|---|---|---|---|---|---|
| | | Shattering[1] | Harvest Maturity[2] | Lodging[3] | Yield[4] |
| 183007-B-10 [2032/B28WT)B-10] (ind1-4/ind1-4) | 2032 [Wild Accession] (ind1-4/ind1-4) | −5 ns | −0.54*** | +0.20 ns | +19 ns |
| 183007-B-10 [2032/B28WT)B-10] (ind1-4/ind1-4) | B28WT [1228/1067-B-28] (IND1 WT) | +20 ns | +0.68*** | −1.00** | −109 ns |
| 183002-B-9 [2032/B3WT)B-9] (ind1-4/ind1-4) | 2032 [Wild Accession] (ind1-4/ind1-4) | +5 ns | −0.04 ns | +0.70** | +39 ns |
| 183002-B-9 [2032/B3WT)B-9] (ind1-4/ind1-4) | B3WT [1036/1228-B-3] (IND1 WT) | +14 ns | +0.48** | −0.17 ns | −32 ns |
| 183012-B-34 [2032/B73WT)B-73] (ind1-4/ind1-4) | 2032 [Wild Accession] (ind1-4/ind1-4) | +4 ns | +0.08 ns | −0.50** | +8 ns |
| 183012-B-34 [2032/B73WT)B-73] (ind1-4/ind1-4) | B73WT [1120/1136-B-73] (IND1 WT) | +20 ns | +0.90*** | −0.94*** | +154** |

[1]Shattering (% of Pods Dehisced at Harvest) at locations demonstrating measurable shattering
[2]Harvest Maturity Rating (1 = Late, 5 = Early) across all locations
[3]Lodging Rating Pre-Harvest (1 = Unharvestable, 5 = Erect) at locations demonstrating measurable lodging
[4]Grain Yield (pounds per acre) across all locations
[5]B28WT and B3WT are commercial genotypes
[6]IND genotype: ind1-4/ind1-4 is homozygous for recessive ind1-4 mutation; IND1 WT is homozygous for wild-type allele.
+indicates difference in desirable direction;
−indicates difference in undesirable direction;
ns indicates no significant difference (t-test);
*indicates t-test significant at alpha = 0.05;
**indicates t-test significant at alpha = 0.01;
***indicates t-test significant at alpha = 0.001 essentially not different from 2032 for shattering resistance. Each of the Gen2 Lines (all homozygous for ind1-4) trend to levels of improvement over their pre-commercial parental control line with data very similar to that shown in Table 13 comparing 2032 itself (homozygous for ind1-4) to B28WT, B3WT and B73WT.

Harvest maturity, lodging, and yield are all examples of quantitative (multigenic) traits which are more difficult to fully capture in progeny in a single generation of breeding. Table 14 shows that the 183007-B-10 line derived from the early line 2032 and the late line B28WT falls between its parents for harvest maturity. In this case the yield of 2032 was retained, but although not statistically significant it appears that we were not able to capture all of the yield of the B28WT parent. This is not an unexpected result. Clearly 2032 conferred shattering resistance and somewhat improved earliness to 183007-B-10 compared to B28WT, but did not capture improved lodging and improved yield from B28WT.

In the case of 183002-B-9, shattering resistance conferred by the recessive ind1-4 mutation of 2032 was captured. In this case most, or all of the earliness conferred by 2032 along with the lodging resistance conferred by the B3WT parent was captured, establishing that earliness and lodging susceptibility are not necessarily linked. Yield was retained at the level of the parents.

In the case of 183012-B-34, the recessive ind1-4 mutation of 2032 again conferred shattering resistance. In this case the earliness conferred by 2032 was captured. However, B73WT is inherently poor for lodging. It is the poorest of the three pre-commercial lines shown in this data. When combined with 2032 we clearly did not capture any synergy between 2032 and B73WT for lodging and in fact lost lodging resistance compared to the better B73WT parent. In these trials 183012-B-34 had equivalent yield to its 2032 parent and improved yield versus B73WT.

In conclusion, this data demonstrates that 2032 is able to pass reduced shattering to its progeny via transmission of the recessive ind1-4 mutation present in the 2032 germplasm. 2032 is also able to confer earlier maturity on progeny although this characteristic is more complex than shattering as shown by the 183007-B-10 results where only partial 2032 earliness is captured. Lodging susceptibility in 2032 is somewhat difficult to overcome as demonstrated by these results although 183002-B-9 results demonstrate that it is possible to overcome 2032 lodging when combined with an acceptable parent and with appropriate selection pressure applied while still capturing earliness and shattering resistance.

Additional data showing transmission of the 2032 early maturity trait is shown in Table 15. In the trial, 46 entries that are the progeny of crosses between 2032 and B3WT or B28WT were tested. Parental 2032, B3WT, and B28WT lines were used as checks for the study. The Growing Degree Units (GDU) and Harvest Maturity data is provided. GDU is a common method of evaluating the amount of heat accumulation plants in the field are subjected to. In this case, GDU accumulation was calculated each day between planting and harvest as follows:

$$[(\text{Daily maximum temperature} + \text{Daily minimum temperature})/2] - 40$$

For background information, 40 is the temperature in Fahrenheit where pennycress plants are believed to stop their development. The warmer the high and/or low of the day, the larger the GDU estimate for that day will be and this is related to the amount of development of the plant on that day. Calculation begins on the day of planting and ends on the day when a plot reaches harvest readiness, as estimated through a drone imagery analysis. Lower numbers indicate earlier maturity.

Harvest Maturity Rating is also provided. This is a 1 to 5 rating made by a member of the breeding team where 4 is ready for harvest, 5 is beyond ready for harvest, and 1 is completely green. Higher numbers indicated earlier harvest readiness than lower numbers.

GDU to 10% Flowering. The flowering date is a different measure that can be used to evaluate maturity of an entry line. The calculation is the same as described for GDU to harvest maturity, except the end date for the calculation is the day on which 10% of plants in a plot are flowering. This date was determined through repeated evaluation of each plot by a member of the breeding team. Lower numbers indicated earlier maturity.

The trial was grown at 3 locations, 2 replications for each. The GDU traits were collected at only 2 locations. There are therefore 4 data plots for GDU to Harvest Maturity and Harvest Maturity Date and 6 data plots for Harvest Maturity Rating and GDU to 10% Flowering.

TABLE 15

| Entry Name [Pedigree] | GDU to Harvest Maturity | | | Harvest Maturity Rating | | | GDU to 10% Flowering | | |
|---|---|---|---|---|---|---|---|---|---|
| | Entry[1] | 2032 | B3 or B28 | Entry[1] | 2032 | B3 or B28 | Entry[1] | 2032 | B3 or B28 |
| 183007-B-1 [2032//B28WT) B-1] | 1663.3 | 1629 | 1719 | 3.33 | 3.67 | 2.33 | 739.67 | 725.33 | 782.4 |
| 183007-B-2 [2032//B28WT) B-2] | 1664 | 1629 | 1719 | 3 | 3.67 | 2.33 | 740.67 | 725.33 | 782.4 |
| 183007-B-3 [2032//B28WT) B-3] | 1657.5 | 1629 | 1719 | 2.67 | 3.67 | 2.33 | 729.83 | 725.33 | 782.4 |
| 183007-B-8 [2032//B28WT) B-8] | 1707.5 | 1629 | 1719 | 2.33 | 3.67 | 2.33 | 752.83 | 725.33 | 782.4 |
| 183007-B-9 [2032//B28WT) B-91 | 1650 | 1629 | 1719 | 3.83 | 3.67 | 2.33 | 733.5 | 725.33 | 782.4 |

TABLE 15-continued

Heritability of Maturity Study

| Entry Name [Pedigree] | GDU to Harvest Maturity | | | Harvest Maturity Rating | | | GDU to 10% Flowering | | |
|---|---|---|---|---|---|---|---|---|---|
| | Entry¹ | 2032 | B3 or B28 | Entry¹ | 2032 | B3 or B28 | Entry¹ | 2032 | B3 or B28 |
| 183007-B-10 [2032//B28WT) B-10] | 1659.5 | 1629 | 1719 | 3.5 | 3.67 | 2.33 | 717 | 725.33 | 782.4 |
| 183007-B-11 [2032//B28WT) B-11] | 1661.3 | 1629 | 1719 | 2.83 | 3.67 | 2.33 | 752.67 | 725.33 | 782.4 |
| 183007-B-13 [2032//B28WT) B-13] | 1662 | 1629 | 1719 | 3.67 | 3.67 | 2.33 | 732.83 | 725.33 | 782.4 |
| 183007-B-14 [2032//B28WT) B-14] | 1660.5 | 1629 | 1719 | 3 | 3.67 | 2.33 | 732.67 | 725.33 | 782.4 |
| 183007-B-15 [2032//B28WT) B-15] | 1655.5 | 1629 | 1719 | 3.33 | 3.67 | 2.33 | 747 | 725.33 | 782.4 |
| 183007-B-17 [2032//B28WT) B-17] | 1774.3 | 1629 | 1719 | 1.5 | 3.67 | 2.33 | 778 | 725.33 | 782.4 |
| 183007-B-18 [2032//B28WT) B-18] | 1665.3 | 1629 | 1719 | 3.33 | 3.67 | 2.33 | 726.67 | 725.33 | 782.4 |
| 183007-B-20 [2032//B28WT) B-20] | 1673.8 | 1629 | 1719 | 3.33 | 3.67 | 2.33 | 730.33 | 725.33 | 782.4 |
| 183007-B-21 [2032//B28WT) B-21] | 1724.3 | 1629 | 1719 | 3 | 3.67 | 2.33 | 732.67 | 725.33 | 782.4 |
| 183007-B-24 [2032//B28WT) B-24] | 1668 | 1629 | 1719 | 3.33 | 3.67 | 2.33 | 734.5 | 725.33 | 782.4 |
| 183007-B-25 [2032//B28WT) B-25] | 1642.3 | 1629 | 1719 | 3.5 | 3.67 | 2.33 | 740 | 725.33 | 782.4 |
| 183007-B-26 [2032//B28WT) B-26] | 1657.5 | 1629 | 1719 | 3.17 | 3.67 | 2.33 | 731.67 | 725.33 | 782.4 |
| 183007-B-29 [2032//B28WT) B-29] | 1714.5 | 1629 | 1719 | 2.33 | 3.67 | 2.33 | 733.5 | 725.33 | 782.4 |
| 183007-B-30 [2032//B28WT) B-30] | 1660.5 | 1629 | 1719 | 3.33 | 3.67 | 2.33 | 745.17 | 725.33 | 782.4 |
| 183007-B-39 [2032//B28WT) B-39] | 1673.8 | 1629 | 1719 | 2.67 | 3.67 | 2.33 | 760.83 | 725.33 | 782.4 |
| 183002-B-1 [2032//B3WT)B-1] | 1631 | 1629 | 1694.5 | 3.83 | 3.67 | 2.5 | 706.3 | 725.33 | 762.83 |
| 183002-B-2 [2032//B3WT)B-2] | 1632 | 1629 | 1694.5 | 3.83 | 3.67 | 2.5 | 725 | 725.33 | 762.83 |
| 183002-B-3 [2032//B3WT)B-3] | 1669 | 1629 | 1694.5 | 2.83 | 3.67 | 2.5 | 733.5 | 725.33 | 762.83 |
| 183002-B-4 [2032//B3WT)B-4] | 1650.8 | 1629 | 1694.5 | 3.5 | 3.67 | 2.5 | 723.5 | 725.33 | 762.83 |
| 183002-B-5 [2032//B3WT)B-5] | 1667 | 1629 | 1694.5 | 3.17 | 3.67 | 2.5 | 734.5 | 725.33 | 762.83 |
| 183002-B-6 [2032//B3WT)B-6] | 1650 | 1629 | 1694.5 | 3.5 | 3.67 | 2.5 | 727.17 | 725.33 | 762.83 |
| 183002-B-7 [2032//B3WT)B-7] | 1665.3 | 1629 | 1694.5 | 2.83 | 3.67 | 2.5 | 720.8 | 725.33 | 762.83 |
| 183002-B-8 [2032//B3WT)B-8] | 1667 | 1629 | 1694.5 | 2.67 | 3.67 | 2.5 | 713.2 | 725.33 | 762.83 |
| 183002-B-9 [2032//B3WT)B-9] | 1647 | 1629 | 1694.5 | 3.67 | 3.67 | 2.5 | 722.7 | 725.33 | 762.83 |

TABLE 15-continued

| | GDU to Harvest Maturity | | | Harvest Maturity Rating | | | GDU to 10% Flowering | | |
|---|---|---|---|---|---|---|---|---|---|
| Entry Name [Pedigree] | Entry[1] | 2032 | B3 or B28 | Entry[1] | 2032 | B3 or B28 | Entry[1] | 2032 | B3 or B28 |
| 183002-B-10 [2032//B3WT)B-10] | 1654.8 | 1629 | 1694.5 | 3.5 | 3.67 | 2.5 | 732.33 | 725.33 | 762.83 |
| 183002-B-11 [2032//B3WT)B-11] | 1659.5 | 1629 | 1694.5 | 3.17 | 3.67 | 2.5 | 719.7 | 725.33 | 762.83 |
| 183002-B-12 [2032//B3WT)B-12] | 1708.8 | 1629 | 1694.5 | 2.17 | 3.67 | 2.5 | 781.33 | 725.33 | 762.83 |
| 183002-B-13 [2032//B3WT)B-131 | 1671 | 1629 | 1694.5 | 3.17 | 3.67 | 2.5 | 730.83 | 725.33 | 762.83 |
| 183002-B-14 [2032//B3WT)B-14] | 1686 | 1629 | 1694.5 | 2.5 | 3.67 | 2.5 | 724.2 | 725.33 | 762.83 |
| 183002-B-15 [2032//B3WT)B-15] | 1657.5 | 1629 | 1694.5 | 2.67 | 3.67 | 2.5 | 732 | 725.33 | 762.83 |
| 183002-B-16 [2032//B3WT)B-16] | 1665.3 | 1629 | 1694.5 | 3.33 | 3.67 | 2.5 | 706.3 | 725.33 | 762.83 |
| 183002-B-17 [2032//B3WT)B-17] | 1651.8 | 1629 | 1694.5 | 3.5 | 3.67 | 2.5 | 718.8 | 725.33 | 762.83 |
| 183002-B-18 [2032//B3WT)B-18] | 1685.8 | 1629 | 1694.5 | 3.17 | 3.67 | 2.5 | 730.5 | 725.33 | 762.83 |
| 183002-B-19 [2032//B3WT)B-19] | 1668 | 1629 | 1694.5 | 2.83 | 3.67 | 2.5 | 731.33 | 725.33 | 762.83 |
| 183002-B-20 [2032//B3WT)B-20] | 1689.5 | 1629 | 1694.5 | 3.33 | 3.67 | 2.5 | 722.8 | 725.33 | 762.83 |
| 183002-B-21 [2032//B3WT)B-21] | 1713.5 | 1629 | 1694.5 | 2 | 3.67 | 2.5 | 750.5 | 725.33 | 762.83 |
| 183002-B-22 [2032//B3WT)B-22] | 1651.8 | 1629 | 1694.5 | 2.83 | 3.67 | 2.5 | 729.83 | 725.33 | 762.83 |
| 183002-B-23 [2032//B3WT)B-23] | 1679.5 | 1629 | 1694.5 | 3 | 3.67 | 2.5 | 735 | 725.33 | 762.83 |
| 183002-B-24 [2032//B3WT)B-24] | 1649 | 1629 | 1694.5 | 3 | 3.67 | 2.5 | 725.3 | 725.33 | 762.83 |
| 183002-B-25 [2032//B3WT)B-25] | 1673.8 | 1629 | 1694.5 | 3.33 | 3.67 | 2.5 | 714.5 | 725.33 | 762.83 |
| 183002-B-26 [2032//B3WT)B-26] | 1631 | 1629 | 1694.5 | 3.33 | 3.67 | 2.5 | 717.3 | 725.33 | 762.83 |
| Mean Difference | | 39.9 | −36.3 | | −0.59 | 0.65 | | 7.3 | −38.7 |
| 2*Error | 76.58 | | | 1.15 | | | 38.93 | | |
| LSD | 53.72 | | | 0.66 | | | 22.21 | | |
| C.V. | 2.29 | | | 18.89 | | | 2.65 | | |
| Error d.f. | 99 | | | 149 | | | 149 | | |
| Prob. Entry | 0.000705433 | | | 0 | | | 0 | | |
| R-Square | 0.69 | | | 0.79 | | | 0.86 | | |
| Total Reps | 4 | | | 6 | | | 6 | | |
| Alpha level | 0.05 | | | 0.05 | | | 0.05 | | |
| Method | RCB | | | RCB | | | RCB | | |

[1]Values in bold and underlined have a 95% probably that the entry is not significantly different from the 2032 parent.

The data in table 15 show on average that the progeny lines are earlier than the B3WT/B28WT parents and a little bit later than the 2032 parent. This result is expected with a quantitative trait like earliness. The consistency with which most of the progeny entries fit this pattern is very strong evidence that the earliness trait was passed from the 2032 parent to its progeny.

What is claimed is:

1. A method of producing a commodity plant product comprising:
   (a) obtaining a plant of *Thlaspi arvense* cultivar 2032, representative seed of *Thlaspi arvense* cultivar 2032 having been deposited under NCMA Accession Number 202210002, or a plant part thereof; and
   (b) producing the commodity plant product from the plant or plant part thereof;
wherein the commodity plant product is an oil, biodegradable plastic, lubricant, biofuel, food or feed product, medicinal product, or a combination thereof.

2. The method of claim 1, wherein a plant part is obtained, wherein the plant part is a seed, and wherein the commodity plant product is oil.

3. The method of claim 1, wherein a plant part is obtained, wherein the plant part is a seed, and wherein the commodity plant product is a biodegradable plastic, biofuel, or feed product.

4. A method of producing a *Thlaspi* plant comprising a reduced seedpod shatter trait and an early maturity time trait, comprising:
   (a) crossing a plant of *Thlaspi arvense* cultivar 2032, representative seed of *Thlaspi arvense* cultivar 2032 having been deposited under NCMA Accession Number 202210002, with a second *Thlaspi* plant to create a population of progeny plants; and
   (b) selecting one or more progeny plants comprising said reduced seedpod shatter trait and said early maturity time trait as compared to said second *Thlaspi* plant when grown under identical environmental conditions.

5. The method of claim 4, wherein the one or more progeny plants are further self-crossed, sibling-crossed, or backcrossed.

6. The method of claim 4, wherein the second *Thlaspi* plant is a commercial variety.

7. A method of harvesting F1 seed, comprising:
   (a) crossing a plant of *Thlaspi arvense* cultivar 2032, representative seed of *Thlaspi arvense* cultivar 2032 having been deposited under NCMA Accession Number 202210002, with a second *Thlaspi* plant; and
   (b) harvesting resulting F1 seed.

* * * * *